(12) United States Patent
Kondo

(10) Patent No.: US 7,102,347 B2
(45) Date of Patent: Sep. 5, 2006

(54) METALLIC CONTAMINANT DETECTING METHOD AND APPARATUS THEREFOR

(75) Inventor: Nobukazu Kondo, Tokyo (JP)

(73) Assignee: Tok Engineering Co., Ltd., Tokyo (JP)

( * ) Notice: Subject to any disclaimer, the term of this patent is extended or adjusted under 35 U.S.C. 154(b) by 0 days.

(21) Appl. No.: 11/131,388

(22) Filed: May 18, 2005

(65) Prior Publication Data

US 2005/0206373 A1    Sep. 22, 2005

Related U.S. Application Data

(62) Division of application No. 10/250,582, filed as application No. PCT/JP02/09601 on Sep. 19, 2002.

(30) Foreign Application Priority Data

Sep. 21, 2001 (JP) ............................. 2001-289924

(51) Int. Cl.
*G01R 33/12* (2006.01)
*G01N 27/72* (2006.01)

(52) U.S. Cl. ...................... 324/239; 324/233

(58) Field of Classification Search ............. 324/228, 324/233, 234, 236, 239, 243, 225, 222, 326; 340/551; 702/116
See application file for complete search history.

(56) References Cited

U.S. PATENT DOCUMENTS

| | | | |
|---|---|---|---|
| 4,584,529 A | 4/1986 | Aoyama | |
| 4,700,139 A | 10/1987 | Podhrasky | |
| 4,868,504 A | 9/1989 | Johnson | |
| 5,304,927 A | 4/1994 | Thomas et al. | |
| 5,523,739 A | 6/1996 | Manneschi | |
| 5,552,705 A | 9/1996 | Keller | |
| 5,923,165 A * | 7/1999 | Horita et al. | ............... 324/239 |
| 5,929,634 A | 7/1999 | Artinger | |
| 5,969,528 A | 10/1999 | Weaver | |
| 6,169,481 B1 | 1/2001 | Goldberg et al. | |
| 6,420,866 B1 | 7/2002 | Goldberg et al. | |
| 6,529,007 B1 | 3/2003 | Ott et al. | |
| 2004/0046550 A1 * | 3/2004 | Kondo | ...................... 324/233 |

FOREIGN PATENT DOCUMENTS

JP    57-8578 U    6/1980

(Continued)

OTHER PUBLICATIONS

International Search Report.

*Primary Examiner*—Edward Lefkowitz
*Assistant Examiner*—Kenneth J. Whittington
(74) *Attorney, Agent, or Firm*—Rader, Fishman & Grauer PLLC

(57) ABSTRACT

A metallic contaminant detecting method and apparatus according to the present invention detect metallic contaminants mixed in objects under inspection, such as food products, pharmaceuticals, and materials for industrial use, which are wrapped in electrically conductive packaging materials, e.g. aluminum. A small magnetic field is generated by applying a voltage to coils (10, 11) or supplying an electric current to the coils. A detection magnetic field generated from a metallic contaminant in response to the small magnetic field is detected as a detection voltage or a detection current of the coils (10, 11), and a detection signal is output. The detection signal is analyzed to detect the metallic contaminant. The small magnetic field is created by applying a small voltage or supplying a small electric current to the coils (10, 11) and using a non-linear portion of the magnetic field characteristics of cores constituting the coils (10, 11).

20 Claims, 17 Drawing Sheets

FOREIGN PATENT DOCUMENTS

| | | |
|---|---|---|
| JP | 56-130652 A1 | 10/1981 |
| JP | 58-018160 A1 | 2/1983 |
| JP | 59160787 | 11/1984 |
| JP | 03-008864 A1 | 1/1991 |
| JP | 03008864 A | 1/1991 |
| JP | 04-116493 A1 | 4/1992 |
| JP | 09-304546 A1 | 11/1997 |
| JP | 11-030607 A1 | 2/1999 |
| JP | 11-258355 A1 | 9/1999 |
| JP | 2000-329858 A1 | 11/2000 |

* cited by examiner

Fig. 11
(a)
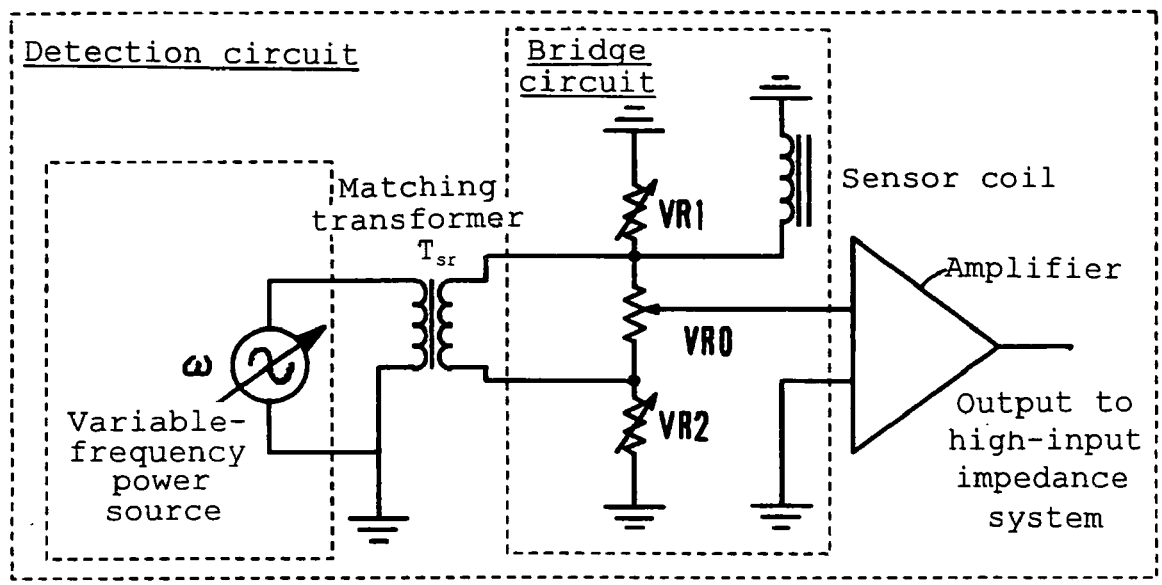
(b)
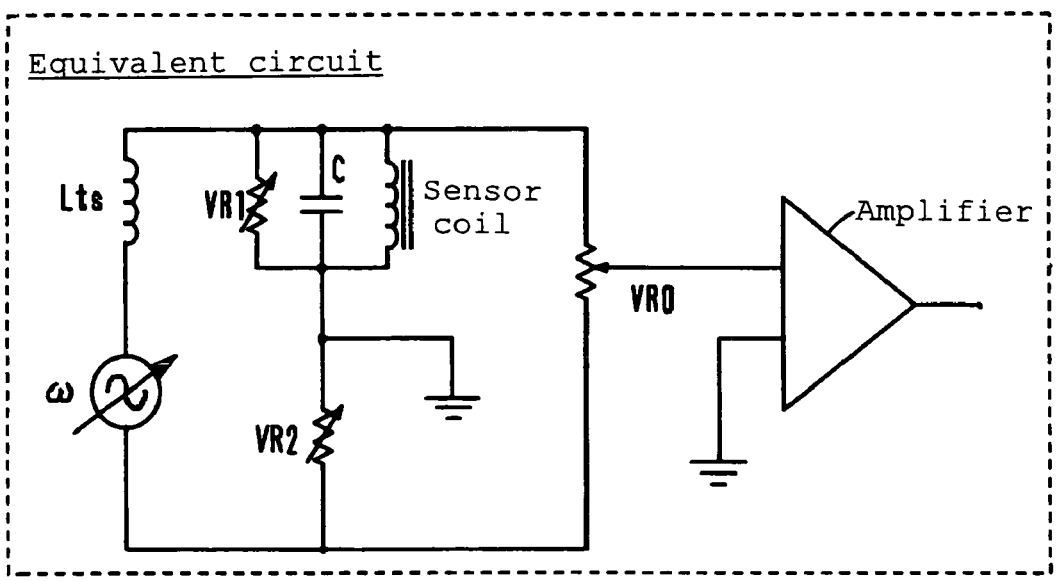

METALLIC CONTAMINANT DETECTING METHOD AND APPARATUS THEREFOR

This application is a divisional application of U.S. Patent Application Ser. No. 10/250,582 filed on Jul. 3, 2003, which is a national stage application of International Application No. PCT/JP02/09601 filed on Sep. 19, 2002, the contents of which are hereby incorporated by reference in its entirety.

TECHNICAL FIELD

The present invention relates to a metallic contaminant detecting apparatus for detecting a metallic contaminant mixed in an object under inspection. More particularly, the present invention relates to a metallic contaminant detecting method and apparatus for detecting metallic contaminants mixed in objects under inspection, such as food products, pharmaceuticals, and materials for industrial use, which are wrapped in electrically conductive packaging materials, e.g. aluminum. Even more particularly, the present invention relates to a metallic contaminant detecting method and apparatus for detecting metallic contaminants in objects under inspection that are in packaging containers or bags formed by vacuum deposition of aluminum or made of aluminum foil or the like.

BACKGROUND ART

Food products, pharmaceuticals, etc. need inspection for contaminants. In the process of manufacturing these products, for example, contaminants such as metal fragments may get mixed in the products. In order to ensure the safety of the products, it is necessary to eliminate metallic contaminants from them and hence essential to detect the metallic contaminants.

Stainless steel is excellent in corrosion resistance and widely used in various products, mainly in the fields of kitchen utensils, building materials, domestic electrical equipment, automotive parts, dairy and fermentation tanks, chemical equipment, thermal insulating apparatus, etc. There are many stainless-steel products particularly in the field of food products, such as food product containers, and structural components, containers and so forth of all machines in food product manufacturing lines and food product manufacturing machines. It is impossible to avoid wear particles or fragments of such stainless steel products getting mixed in food products. Stainless steels are alloy steels exhibiting excellent corrosion resistance.

Stainless steels are roughly divided into austenite stainless steels, martensite stainless steels, and ferrite stainless steels. It is known that these stainless steels exhibit magnetic properties. Therefore, various kinds of stainless steel can be detected as metallic contaminants by using their characteristic properties.

CONVENTIONAL DETECTION TECHNIQUE

A sensor coil comprising a core and a copper wire wound around the core has heretofore frequently been used to detect a metallic contaminant. That is, a magnetic field is generated by the sensor coil, and an influence on the magnetic field exerted by a metallic substance when passing through the magnetic field is sensed to detect the metallic substance. More specifically, the conventional sensor coil comprises a magnetic field generating coil for generating a magnetic field and a magnetic field receiving coil for receiving the magnetic field. The magnetic field generating coil and the magnetic field receiving coil are disposed to face each other, and an inspection object is passed between them to detect a possible metallic contaminant.

The magnetic field receiving coil receives a magnetic field induced by an eddy current flowing through a metallic substance. For the receiving coil, it is easy to receive a large magnetic field. FIG. 6 shows a B-H characteristic graph ("magnetic flux density" to "magnetic field"), which is the magnetic history curve (magnetization intensity - magnetizing force) of the core constituting the receiving coil. It is general practice to use the linear region $P_2$ or the relaxation region $P_3$ of the magnetic history curve for the detection of a metallic contaminant by use of the above-described magnetic field generating coil.

A strong magnetic field produces a large magnetic flux. This causes a large eddy current to flow through a metallic substance contained in the inspection object. Thus, a large magnetic field induced by the eddy current is received by the magnetic field receiving coil. In many cases, the above-described magnetic field generating coil transmits an electromagnetic wave in the frequency band of 1 MHz to 333 kHz to the inspection object, and the magnetic field receiving coil, which is installed at the opposite side of the inspection object, detects the electromagnetic wave to identify a metallic contaminant.

The electromagnetic wave consists of a component passing through the inspection object; a component reflected by the inspection object; and a component absorbed by the inspection object. When the inspection object is small in size, the detection sensitivity is increased by generating as a strong electromagnetic wave as possible. For this purpose, the frequency of the electromagnetic wave may be increased. As the frequency becomes higher, the proportion of the reflective component increases. This may cause the reception sensitivity to be degraded, conversely.

Many of food products, pharmaceuticals, etc. are packaged in the manufacturing process and shipped in the packaged state. Packages are made of paper, aluminum and other various kinds of materials. However, it has been difficult to detect metallic contaminants in food products in packaging bags or containers made of electrically conductive materials, such as aluminum pouches or films, by using the conventional sensor coil. The reason for this is that an eddy current is produced in the containers as the magnetic field becomes strong, thus making it difficult to detect metallic contaminants in the containers.

For this reason, an X-ray apparatus is used to detect metallic contaminants in packaging bags or containers. An inspection object is irradiated with X-rays by the X-ray apparatus, and X-rays passing through the inspection object are received by a film or a detector for image projection placed at the opposite side of the inspection object. The received image is processed to judge the presence of a metallic contaminant. In other words, strong X-rays are passed through a packaging bag made of an electrically conductive material, and the transmitted X-rays are received. Then, image data obtained from the received X-rays is subjected to image processing to detect and identify a metallic contaminant.

This detection method suffers unfavorably low detection accuracy (the method can detect only bolts or nuts, for example, which have a diameter not less than about 6 millimeters or 8 millimeters). In addition, there is a danger that the operator of the X-ray apparatus may be exposed to X-rays. There are many other problems. That is, the X-ray apparatus is large in size and costs a great deal to maintain. In the case of a packaging bag having a food product or the like sealed therein, the end and central portions of the bag are different in thickness from each other. Consequently, the amount of X-rays transmitted differs according to the thickness. Accordingly, even if X-rays of the same intensity are applied to the end and central portions of the packaging bag, the transmitted X-rays are different in intensity. Therefore, it is difficult to detect a metallic contaminant with high accuracy.

There has also been proposed a technique of identifying the kind of metal by using a sensor coil. A sensor apparatus disclosed in Japanese Patent Application Post-Exam Publication No. Hei 3-18143 can identify the kind of metal passing in the neighborhood of a sensor coil by using a resonant circuit. Because the voltage output from the resonant circuit varies according to the kind of metals, e.g. copper, aluminum, and iron, the kind of metal can be distinguished. Japanese Patent Application Unexamined Publication (KOKAI) No. 2000-329858 discloses a metallic contaminant detecting apparatus having a magnetic sensor comprising a resonant circuit.

However, the conventionally proposed metallic contaminant detection using a sensor coil cannot efficiently detect small metal fragments as metallic contaminants of the order of several millimeters in size because of low detection sensitivity. It is also difficult to detect metallic contaminants in packaging bags or containers made of an electrically conductive material such as aluminum. The reason for this is that a signal generated from a packaging bag or container made of an electrically conductive material is so large that it cannot be distinguished from a signal derived from a metallic contaminant.

With the above-described technical background, the present invention was made to attain the following objects.

An object of the present invention is to provide a metallic contaminant detecting method and apparatus for detecting a metallic contaminant in a packaging bag or container made of an electrically conductive material by using a magnetic field.

Another object of the present invention is to provide a metallic contaminant detecting method and apparatus capable of detecting a small-sized metallic contaminant in a packaging bag or container made of an electrically conductive material, e.g. aluminum, with high sensitivity.

Still another object of the present invention is to provide a metallic contaminant detecting method and apparatus using a detection circuit or a signal processing circuit capable of effectively detecting a small magnetic field to detect the above-described small-sized metallic contaminant with high sensitivity.

An advantage of the metallic contaminant detecting apparatus according to the present invention resides in that a metallic contaminant can be detected with high sensitivity by setting an increased Q-value for a bridge circuit having a sensor coil, a variable-frequency power source and a variable resistor. Setting an increased Q-value causes the current in the detection circuit to have a large phase shift, so that a metallic contaminant generating a small magnetic field can be detected with high sensitivity.

Another advantage of the metallic contaminant detecting apparatus according to the present invention is the capability to detect a metallic contaminant in a packaging bag or container made of an electrically conductive material, e.g. aluminum, in particular. The resonance condition of the detection circuit can be controlled to obtain a large Q-value by adjusting the supply frequency through the variable resistor and the variable-frequency power source. Thus, it becomes possible to adjust the whole circuit smoothly.

DISCLOSURE OF THE INVENTION

The present invention is applied to a metallic contaminant detecting method comprising:

a conveying step of conveying an inspection object contained in a package along a conveyance path to detect a metallic contaminant accidentally mixed in the inspection object during a manufacturing process; and a metallic contaminant detecting step of detecting the metallic contaminant mixed in the inspection object by generating a magnetic field from a detecting element provided in an intermediate portion of the conveyance path, the detecting element having a coil comprising a core and a conductor wound around the core.

According to the present invention, the metallic contaminant detecting method comprises:

a detection signal outputting step of generating a small magnetic field by applying a voltage to the coil or supplying an electric current to the coil, and detecting a detection magnetic field generated from the metallic contaminant in response to the small magnetic field as a detection voltage or a detection current of the coil, and then outputting a detection signal; and a signal analyzing step of analyzing the detection signal to identify the metallic contaminant.

In the metallic contaminant detecting method, the small magnetic field is created by applying a small voltage to the coil or supplying a small electric current to the coil and using a non-linear portion of magnetic field characteristics of the core constituting the coil.

The detecting element is preferably arranged to output the detection signal when the metallic contaminant affects the detection magnetic field so as to change a condition of the coil. Preferably, the inspection object has a package made of an electrically conductive material, and an eddy current induced in the electrically conductive material by the small magnetic field is so small that the eddy current does not substantially affect the voltage or electric current flowing through the coil.

The signal analyzing step comprises adding together the detection signal and a phase-inverted signal obtained by phase-inverting an AC excitation power source causing the coil to generate the small magnetic field, thereby eliminating a signal derived from the AC excitation power source from the detection signal, and taking out a signal above a predetermined threshold value, thereby separating a magnetic field signal derived from the inspection object from the detection signal.

Preferably, the metallic contaminant detecting step comprises a first detecting step and a second detecting step. The first detecting step and the second detecting step are arranged so that the inspection object passes through the second detecting step after passing through the first detecting step. The detection signal that is detected simultaneously by the first detecting step and the second detecting step is eliminated by the signal analyzing step.

By this eliminating process, the influence of noise generated from peripheral equipment or the like can be removed. It is preferable to provide a magnetizing step having a magnet booster comprising magnet elements in the conveyance path to magnetize the metallic contaminant before the metallic contaminant detecting step. The magnet booster magnetizes the metallic contaminant so that a magnetic field from the metallic contaminant can be detected even more surely.

The package may be made of any of paramagnetic metals such as aluminum metal, chromium, and manganese, or diamagnetic metals such as copper, silver, and gold. The metallic contaminant may be an alloy such as an austenite or martensite stainless steel material. Preferably, the coil operates at a frequency in the range of from several hundred Hz to several ten kHz. With such a low frequency, it is unlikely that an eddy current will be induced on the surface of the package. Accordingly, a metallic contaminant in the inspection object can be detected with high sensitivity.

Preferably, the detecting element has a first coil and a second coil and comprises a first circuit that is an oscillation circuit including the first coil, and a second circuit that is an oscillation circuit including the second coil. The first circuit and the second circuit are connected in parallel.

Preferably, the first coil for detecting one surface of the inspection object and the second coil for detecting another surface of the inspection object opposite to the one surface are disposed at a predetermined angle with respect to the traveling direction of the inspection object, and the first coil and the second coil are disposed with a predetermined angle with respect to each other.

Preferably, the magnet booster comprises at least two constituent parts disposed at respective positions facing each other across the conveyance path, and the magnet elements forming the two constituent parts are disposed in such a manner that like magnetic poles thereof face toward the conveyance path.

In addition, the present invention is applied to a metallic contaminant detecting apparatus comprising:

conveying means having a conveyance path for conveying an inspection object contained in a package to detect a metallic contaminant accidentally mixed in the inspection object during a manufacturing process; and metallic contaminant detecting means for detecting the metallic contaminant mixed in the inspection object by generating a magnetic field from a detecting element provided in an intermediate portion of the conveyance path, the detecting element having a coil comprising a core and a conductor wound around the core.

According to the present invention, the metallic contaminant detecting apparatus comprises:

detection signal outputting means for generating a small magnetic field by applying a voltage to the coil or supplying an electric current to the coil, and for detecting a detection magnetic field generated from the metallic contaminant in response to the small magnetic field as a detection voltage or a detection current of the coil and outputting a detection signal; and signal analyzing means for analyzing the detection signal to identify the metallic contaminant.

In the metallic contaminant detecting apparatus, the small magnetic field is created by applying a small voltage to the coil or supplying a small electric current to the coil and using a non-linear portion of magnetic field characteristics of the core constituting the coil.

The detecting element is preferably arranged to output the detection signal when the metallic contaminant affects the detection magnetic field so as to change a condition of the coil. Preferably, the inspection object has a package made of an electrically conductive material, and an eddy current induced in the electrically conductive material by the small magnetic field is so small that the eddy current does not substantially affect the voltage or electric current flowing through the coil.

Preferably, the signal analyzing means adds together the detection signal and a phase-inverted signal obtained by phase-inverting an AC excitation power source causing the coil to generate the small magnetic field, thereby eliminating a signal derived from the AC excitation power source from the detection signal, and takes out a signal above a predetermined threshold value, thereby separating a magnetic field signal derived from the inspection object from the detection signal.

Preferably, the metallic contaminant detecting means comprises first detecting means and second detecting means. The first detecting means and the second detecting means are arranged so that the inspection object passes through the second detecting means after passing through the first detecting means. The detection signal that is detected simultaneously by the first detecting means and the second detecting means is eliminated by the signal analyzing means.

Preferably, a magnet booster comprising magnet elements is disposed in the conveyance path upstream of the metallic contaminant detecting means. The magnetizing means magnetizes the metallic contaminant, thus enabling the detection sensitivity to be increased.

Detection can be effected even if the package is made of any of paramagnetic metals such as aluminum, chromium, and manganese, or diamagnetic metals such as copper, silver, and gold. The electric current or voltage supplied to the coil has a frequency in the range of from several hundred Hz to several ten kHz. The frequency changes when the metallic contaminant passes near the coil.

The detecting element is characterized by having a first coil and a second coil and comprising a first circuit that is an oscillation circuit including the first coil, and a second circuit that is an oscillation circuit including the second coil. The first circuit and the second circuit are connected in parallel.

The arrangement may be such that the first coil for detecting one surface of the inspection object and the second coil for detecting another surface of the inspection object opposite to the one surface are disposed at a predetermined angle with respect to the traveling direction of the inspection object, and the first coil and the second coil are disposed with a predetermined angle with respect to each other.

Preferably, the magnet booster comprises at least two constituent parts disposed at respective positions facing each other across the conveyance path, and the magnet elements forming the two constituent parts are disposed in such a manner that like magnetic poles thereof face toward the conveyance path.

First, the outline of the metallic contaminant detection principle of the present invention will be described below.

(Detection Principle)

A detection circuit for detecting a metallic contaminant in the present invention is shown in FIG. 11(*a*). The detection circuit is supplied with electric energy from a variable-frequency power source through a matching transformer $T_{sr}$. The detection circuit includes a bridge circuit having a sensor coil. The sensor coil serves as one arm of a balanced or unbalanced bridge circuit. The sensor coil comprises a core and a coil wound around the core.

The sensor coil assumes the most important role in the detection circuit. The sensor coil has both the function of radiating an alternating magnetic field directly in the vicinity of the coil detection surface by an alternating current supplied thereto from the variable-frequency power source and the function of detecting a turbulent magnetic field when an inspection object having a small metal fragment disorders the orientation of the alternating magnetic field and of generating an output as a contaminant detecting signal.

Finally, the output from the bridge circuit is amplified through an amplifier and delivered to a subsequent circuit.

An electric energy of frequency ω from the variable-frequency power source is supplied across a variable resistor $VR_0$ of the bridge circuit through the matching transformer $T_{sr}$. The bridge circuit is isolated from the variable-frequency power source by the matching transformer $T_{sr}$. One end of the sensor coil is connected to one end of the variable resistor $VR_0$. The other end of the sensor coil is grounded.

The detection circuit can be expressed as an equivalent circuit shown in FIG. 11 (b). The capacitor C shown in FIG. 11(b) is the stray capacitance of the sensor coil, which is not shown in FIG. 11(a). A capacitor can be additionally installed in parallel to the sensor coil for the convenience of adjustment of the circuit and so forth. The inductance $L_{ts}$ in FIG. 11(b) is the self-inductance and mutual inductance of the matching transformer $T_{sr}$ as expressed in terms of the secondary inductance.

The equivalent circuit in FIG. 11(b) may be regarded as equivalent to a constant-current driving circuit shown in FIG. 12(a) or to a constant-voltage driving circuit shown in FIG. 12(b) according to the functional arrangement of the variable-frequency power source. The constant-current driving circuit in FIG. 12(a) assumes a case where the variable-frequency power source supplies electric energy from the transistor collector output or the like (constant-current source). The constant-voltage driving circuit in FIG. 12(b) assumes a case where the detection circuit is driven by a low-output impedance circuit, e.g. an OP amplifier (constant-voltage source).

The value of the inductance L and the value of the capacitor C are constant values determined by the structure and material of the sensor coil and so forth. If the frequency ω of the variable-frequency power source is changed with the value of the variable resistor VR fixed at an arbitrary value, this circuit resonates at a certain frequency $\omega_0$. This can be explained by using a quality factor value Q, which is often used as an index of resonance characteristics of a circuit.

(Calculation of Characteristics)

The resonant frequency can be expressed by equation 1, and the impedance Z, which is determined by the ratio of L to C, can be expressed by equation 2.

For example, when VR is 1 kΩ and Z=1 kΩ, the value of the quality factor Q is 1 (Q=1).

$$f_R = \frac{1}{2\Pi\sqrt{LC}} \quad [\text{Eq. 1}]$$

$$z = \sqrt{\frac{L}{C}} \quad [\text{Eq. 2}]$$

When the Q-value is relatively small, the value of VR can be calculated from the required Q according to equation 3:

$$VR \approx Q \cdot Z \quad [\text{Eq. 3}]$$

Graph 1 in FIG. 17(a) shows characteristics plotted for each frequency when the value of VR is stepwise changed so that the resistance value is increased in order from $VR_1$, to $VR_6$, by way of example. The ordinate axis shows the impedance Z on a log scale. In the graph 1, the normalized frequency 4 is assumed to be a resonant frequency. It will be understood from the graph 1 that the resonance characteristics become steeper as the value of the resistor VR is increased.

Graph 2 in FIG. 17(b) shows similar phase characteristics. As the Q-value increases, i.e. as the value of VR increases, the phase change with respect to frequency increases. The present invention utilizes the characteristics that a large phase shift occurs when the Q-value of the detection circuit is set large, as will be understood from the graphs 1 and 2. The inductance L and the stray capacitance C are constant values that are determined from the material and characteristics of the sensor coil. The inductance L includes the inductance of the matching transformer $T_{sr}$ expressed in terms of the secondary inductance, and the mutual inductance.

Accordingly, it is possible to set a large Q-value by varying the frequency of the supply power source and the variable resistor value VR. In actuality, a Q-value is set in accordance with the size of metallic contaminants to be detected, the frequency of the supply power source, other elements of the circuit, the characteristics of a post-stage circuit and an amplifier, etc. When the bridge circuit of the detection circuit is unbalanced, the detection circuit constantly delivers an output even when there is no metallic contaminant to be detected. The output of the detection circuit is removed in the post-stage circuit by inverting the phase of the power source frequency. This is carried out by using a differential amplifier or the like.

Further, in the present invention, the electric current flowing through the sensor coil is set small. That is, as shown in FIG. 6, the present invention uses a region $P_1$, of the B-H characteristics of the core constituting the sensor coil. This region is a non-linear portion where both the magnetic field H and the magnetic flux density B are small. The use of this region allows detection of satisfactory sensitivity even when a metallic contaminant in the inspection object is small in size.

(Regarding Small Magnetic Field)

Let us consider a case where an inspection object passes near the coil at a constant passing speed and at a constant temperature. Typical causes of changing the electric current in the sensor coil are the eddy current, permeability and dielectric constant of the inspection object and the magnitude of speed at which the inspection object passes near the sensor coil. It is presumed that among these causes, the permeability of the metallic contaminant has the most significant effect on the electric current. The reason for this is as follows. In a case where a metallic contaminant in the inspection object is made of a material having a high permeability, the permeability of the metallic contaminant has a significant effect on the change in magnetic field of the sensor coil when the above-described small electric current is supplied to the sensor coil.

Table 1 below shows the relative permeability of metallic substances. As shown in Table 1, the relative permeability of metals varies widely according to the kind thereof. The relative permeability of metals such as iron, stainless steel, nickel and cobalt is from several hundreds to several tens of thousands. When a small magnetic field is applied to a metal having a small relative permeability, such as aluminum, to such an extent that no eddy current is induced in the metal, the reaction of a metal of large relative permeability wrapped in aluminum or the like is so strong as to affect the magnetic field generated from the sensor coil.

TABLE 1

Relative Permeability of Metallic Substances

| Metal | Permeability (air 1) | Metal | Permeability |
|---|---|---|---|
| aluminum | 1 | stainless steel (austenite) | 3 to 4 to 5 (pure material) |
| copper | 1 | stainless steel (standard material of different composition) | 50 to 200 |
| iron | 500 to 20,000 | nickel | 250 |
| stainless steel (martensite) | 300 to 600 | cobalt | 300 |

In the present invention, a metallic contaminant is detected by using a phase shift of the electric current flowing through the sensor coil. However, it is also possible to detect a metallic contaminant by measuring the voltage applied to the sensor coil or the impedance instead of using the phase shift. In the following, the invention using the electric current flowing through the sensor coil as a detection signal will be described.

Further, the present invention uses a frequency in the audio-frequency range of from several hundred Hz to several ten kHz as a frequency supplied from the variable-frequency power source to the detection circuit. More specifically, the detection circuit is supplied with a power of a frequency in the neighborhood of 4.5 kHz or 7 kHz. The use of such a low frequency minimizes the eddy current induced in the metallic substance under detection by the alternating magnetic field. Consequently, the effect of the eddy current on the original alternating magnetic field reduces to such an extent that it is almost ignorable.

(Consideration of Phase Shift)

Here, let us explain the phase shift. In a case where an active circuit is connected to the input/output end of a passive analog circuit, it is necessary to grasp a standing wave as a steady-state phenomenon from the viewpoint of signal transmission and noise generation. Let us assume a case where the driver-side low-output impedance is connected to the receiver-side high-input impedance circuit. This is equivalent to a case where high-gain OP amplifiers are connected to each other through long wiring, or a case where a passive circuit having a large inductance, which is isolated by a matching transformer $T_{sr}$, is connected as in the case of the bridge circuit in the embodiment of this invention.

If a terminating resistor is inserted on the receiver side to eliminate reflections, the signal travels at a constant speed, and the phase shifts sequentially according to measuring points. Usually, however, connection is made between circuit elements. Therefore, the circuit is not terminated. Moreover, it is not always easy to obtain matching (complete matching). For these reasons, reflections occur. Thus, the signal reciprocates many times because of the reflections. Consequently, resonance occurs, and a standing wave is generated. Thus, the signal vibrates as a whole to a considerable extent with the amplitude of the standing wave. This is understood as amplitude modulation.

At this time, signals in various portions move simultaneously and are equal in phase to each other. Hence, wave propagation does not occur. This is a standing wave. Regarding resonance conditions, the resonance occurs when the length of a signal line concerning the signal that is routed to form the circuit is one-quarter of the wavelength of the signal. The resonance also occurs at a frequency that is an odd number times the signal frequency. In the detecting element of the present invention that is in a resonant state, a sensor coil voltage (or current) of several kHz for producing a magnetic field is amplitude-modulated by the standing wave (of the order of from 0.2 Hz to 2 Hz).

BRIEF DESCRIPTION OF THE DRAWINGS

FIGS. 3(a), (b) and (c) are diagrams showing a sensor coil 10a, of which: FIG. 3(a) is a front view; FIG. 3(c) is a plan view; and FIG. 3(c) is a sectional view taken along the line A—A in FIG. 3(a).

FIGS. 11(a) and (b) show the detection circuit according to embodiment 1 of the present invention, of which: FIG. 11(a) shows the outline of the detection circuit; and FIG. 11(b) is a diagram showing an equivalent circuit of the detection circuit.

BEST MODE FOR CARRYING OUT THE INVENTION

[Embodiment 1 of the Invention]

(Structure of Metallic Contaminant Detecting Apparatus)

Figure 1:
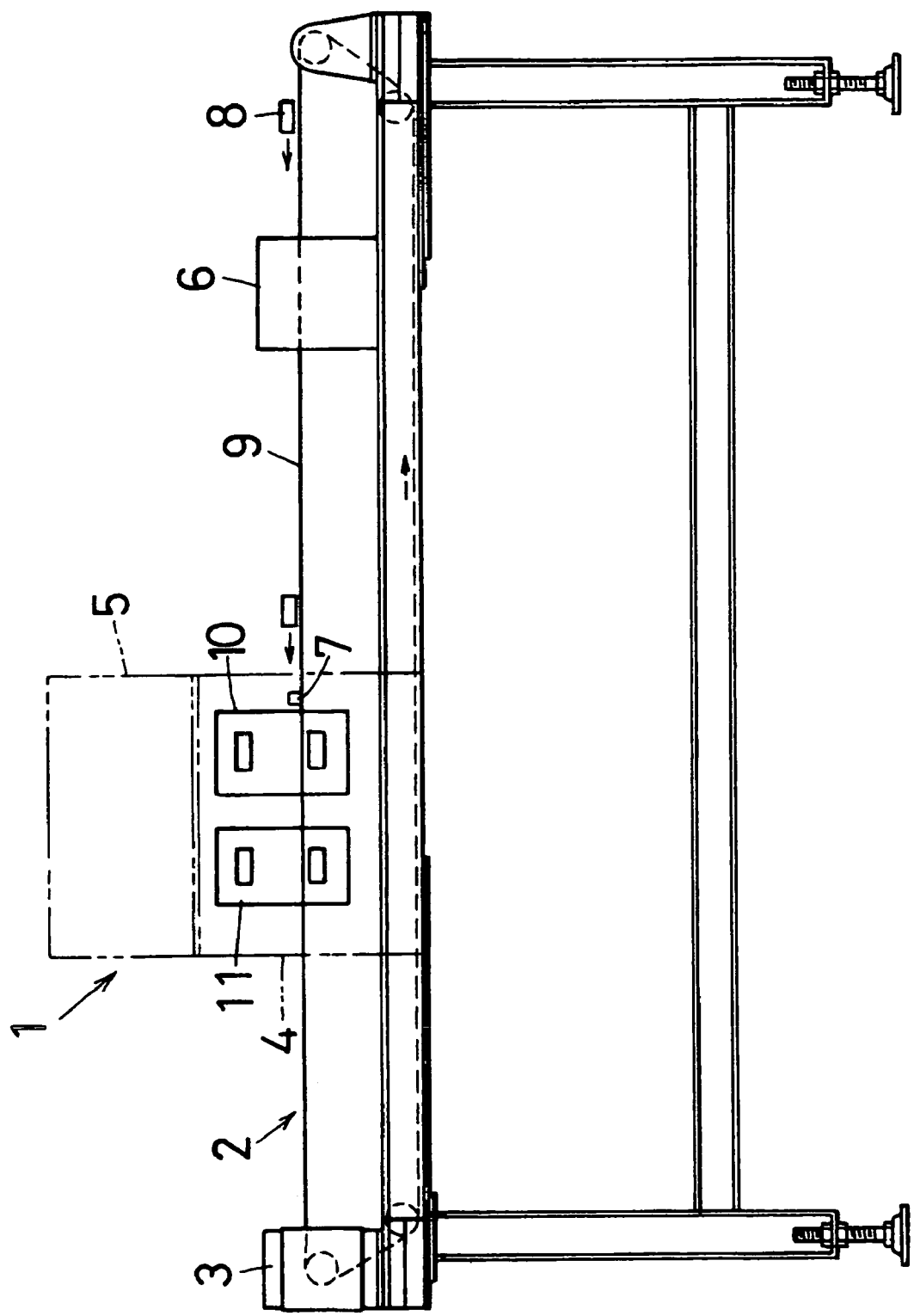
FIG. 1 is a schematic view of a metallic contaminant detecting apparatus 1.

FIG. 1 shows schematically a metallic contaminant detecting apparatus 1. The metallic contaminant detecting apparatus 1 is adapted to detect a metallic contaminant in an object under inspection, particularly a metallic contaminant mixed in a food product in an aluminum packaging bag, which is a container for wrapping a food product, and to give notice of the detected fact. The metallic contaminant detecting apparatus 1 comprises a belt conveyor 2, a motor 3 for driving, a sensor storage part 4, a control part 5, a magnet booster 6, and so forth. The belt conveyor 2 is a belt conveyor device mounted on a legged frame and adapted to convey an object 8 under inspection at a predetermined speed.

The belt conveyor 2 has an endless belt 9 that is driven to rotate by a driving motor 3 provided at one end of the belt conveyor 2. An object 8 under inspection is conveyed on the belt 9. In the conveyance path along which the inspection object 8 is conveyed, a sensor storage part 4 is disposed in the vicinity of the center of the belt 9 in the longitudinal direction thereof. The sensor storage part 4 contains a first sensor coil 10, a second sensor coil 11, an optical sensor 7, etc. for detecting a metallic contaminant in the inspection object.

An output signal from the sensor storage part 4 is sent to a control part 5. The first sensor coil 10 and the second sensor coil 11 have the same structure (a detailed description thereof will be made later). The control part 5 analyzes the signal from the sensor storage part 4 to judge whether or not a metallic contaminant is present in the inspection object, and gives notice (warning sound, display, etc.) of the result of the judgment. As shown in FIG. 1, the control part 5 is installed on top of the sensor storage part 4 in this embodiment.

The inspection object 8 on the belt conveyor 2 is conveyed to the sensor storage part 4 through a magnet booster 6. The magnet booster 6 is disposed upstream of the sensor storage part 4 (as viewed in the traveling direction). The magnet booster 6 is an auxiliary magnetization device for magnetizing a metallic contaminant that may be present in the inspection object. As the inspection object 8 passes through the magnet booster 6, the degree of magnetization of a magnetic substance in the inspection object is increased. Consequently, the detection sensitivity at the sensor storage part 4 increases.

The optical sensor 7 is installed upstream of the first sensor coil 10 to detect the timing at which the inspection object being conveyed enters the first sensor coil 10. The optical sensor 7 transmits information about the detected timing to the control part 5. As the driving motor 3 is started, the belt 9 of the belt conveyor 2 is driven to rotate. At this time, an inspection object is placed on the belt 9 at a loading side, i.e. at one end of the belt 9, and conveyed toward the other end of the belt 9. While being conveyed on the belt 9, the inspection object passes through the magnet booster 6 and enters the sensor storage part 4.

The optical sensor 7 detects the inspection object and informs the control part 5 of the timing at which the inspection object enters the first sensor coil 10. On receipt of the information from the optical sensor 7, the control part 5 analyzes output signals from the first and second sensor coils 10 and 11 delivered when the inspection object passes through each sensor coil, to detect the presence or absence of a metallic contaminant in the inspection object. If a metallic contaminant is contained in the inspection object, the control part 5 outputs a signal indicating the detected fact. The output signal is sent to an electrically driven arm or the like disposed in or connected to the metallic contaminant detecting apparatus 1 to perform necessary processing, e.g. removal of the inspection object containing a metallic contaminant by the electrically driven arm or the like.

The control part 5 does not always need to be installed on top of the sensor storage part 4 but may be placed in any environment where the control part 5 can receive and process signals from the sensor storage part 4. To detect the speed of the belt 9 being driven, the control part 5 needs to be capable of receiving a signal indicating the rotational speed or the like of the driving motor 3. The optical sensor 7 may be of any publicly known type and configuration, provided that the optical sensor used can detect the timing at which the inspection object enters the first sensor coil 10.

Figure 2:
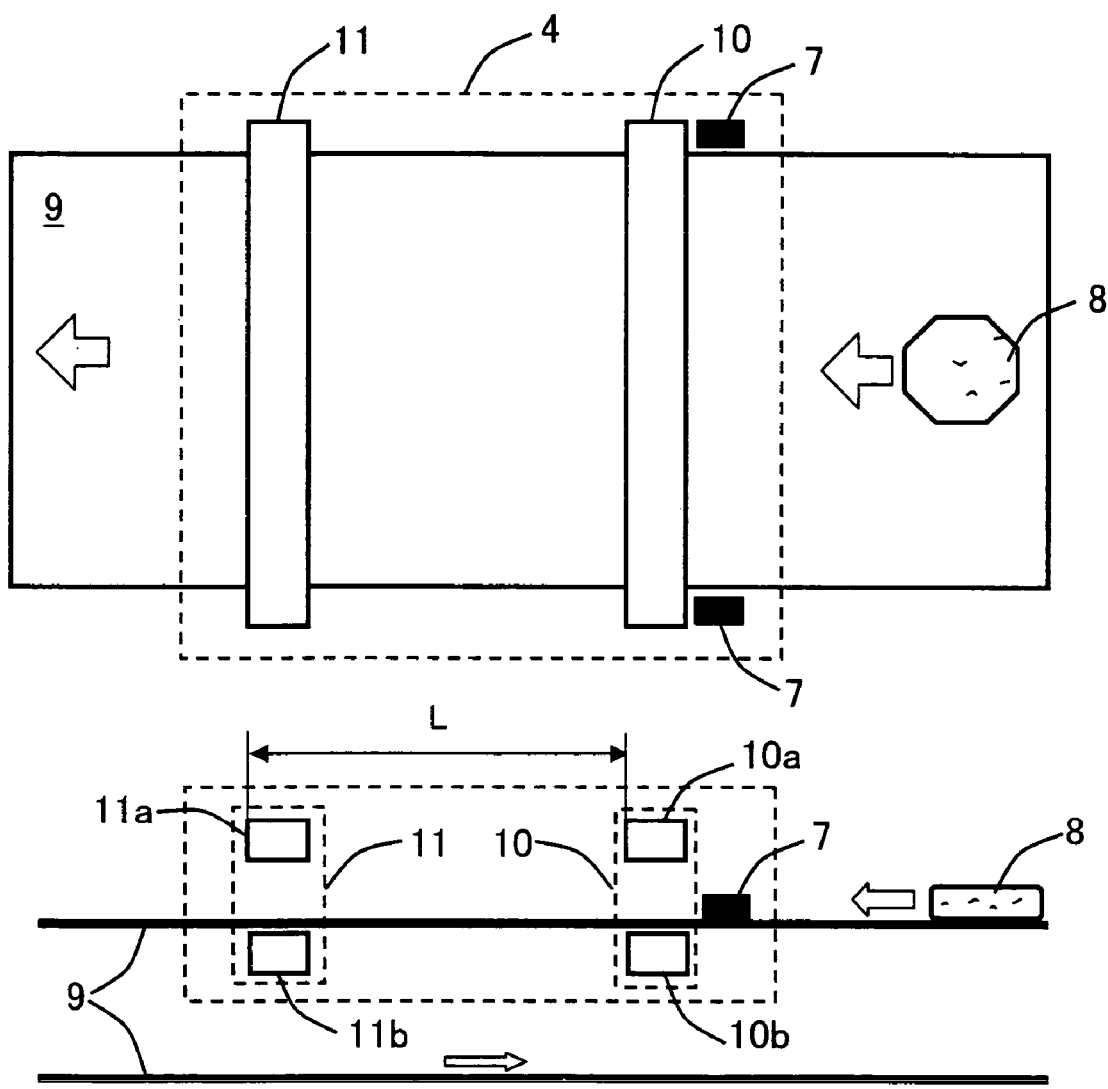
FIG. 2 is a diagram showing a structural example of a sensor storage part 4.

FIG. 2 shows schematically the sensor storage part 4. The sensor storage part 4 comprises a first sensor coil 10 and a second sensor coil 11. The first sensor coil 10 comprises a sensor coil 10a and a sensor coil 10b, which are disposed to face each other vertically across the belt 9. Similarly, the second sensor coil 11 comprises a sensor coil 11a and a sensor coil 11b, which are disposed facing each other.

Figure 3:
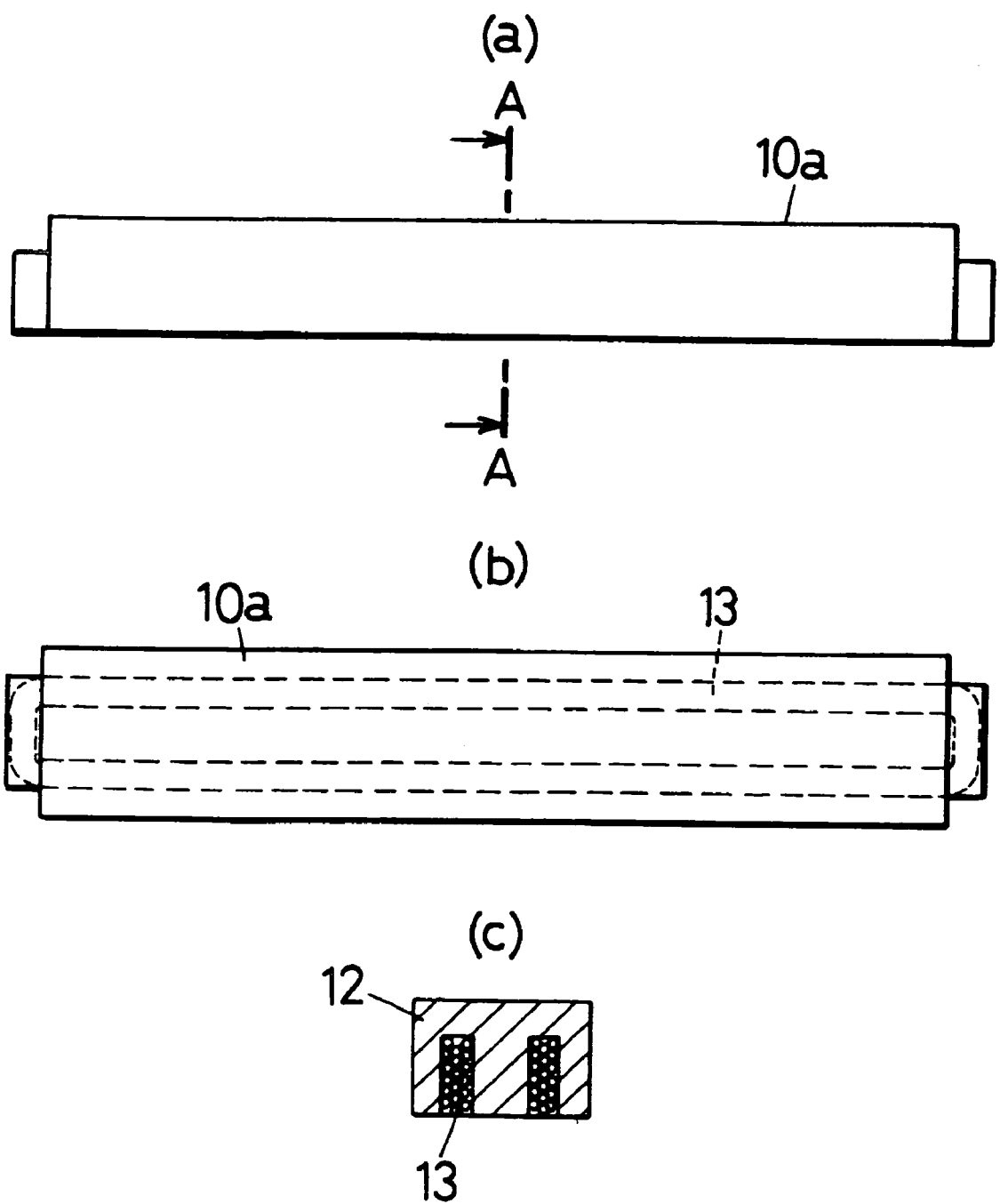

The first sensor coil 10 and the second sensor coil 11 are installed at a distance L away from each other along the belt 9. The sensor coils 10a, 10b, 11a and 11b have basically the same configuration, i.e. an elongated box-shaped configuration as shown in FIG. 3, and are fixedly disposed parallel to the surface of the belt 9 so as to extend perpendicularly to the conveying direction of the belt 9.

The optical sensor 7 is installed upstream of the first sensor coil 10 as viewed in the conveying direction. The optical sensor 7 is necessary for determining the timing at which the inspection object is entered into the first sensor coil 10. The timing at which the inspection object is entered into the second sensor coil 11 can be calculated from the timing at which the inspection object was entered into the first sensor coil 10, the distance L and the conveying speed of the belt 9. The conveying speed of the belt 9 can be calculated from the rotational speed of the driving motor 3. It should be noted that the method of calculating the timing is a well-known technique and not the gist of the present invention. Therefore, a description thereof is omitted.

The sensor coils 10a and 11a are adapted to detect mainly the upper portion of an inspection object flowing on the belt 9. The sensor coils 10a and 11a are installed over the belt 9 with a predetermined gap therefrom to allow the inspection object to pass therethrough. The sensor coils 10b and 11b are adapted to detect mainly the lower portion of the inspection object and hence installed under the belt 9.

FIGS. 3(a) and 3(b) show the structure of a sensor coil. Because the sensor coils 10a, 10b, 11a and 11b have substantially the same structure, only the sensor coil 10a is illustrated and will be described below. The sensor coil 10a has a core 12 made of an electrically conductive material. The core 12 has an elongated box-shaped configuration with an E-shaped sectional structure. The core 12 has a coil 13 wound along the groove portion thereof.

Figure 4:
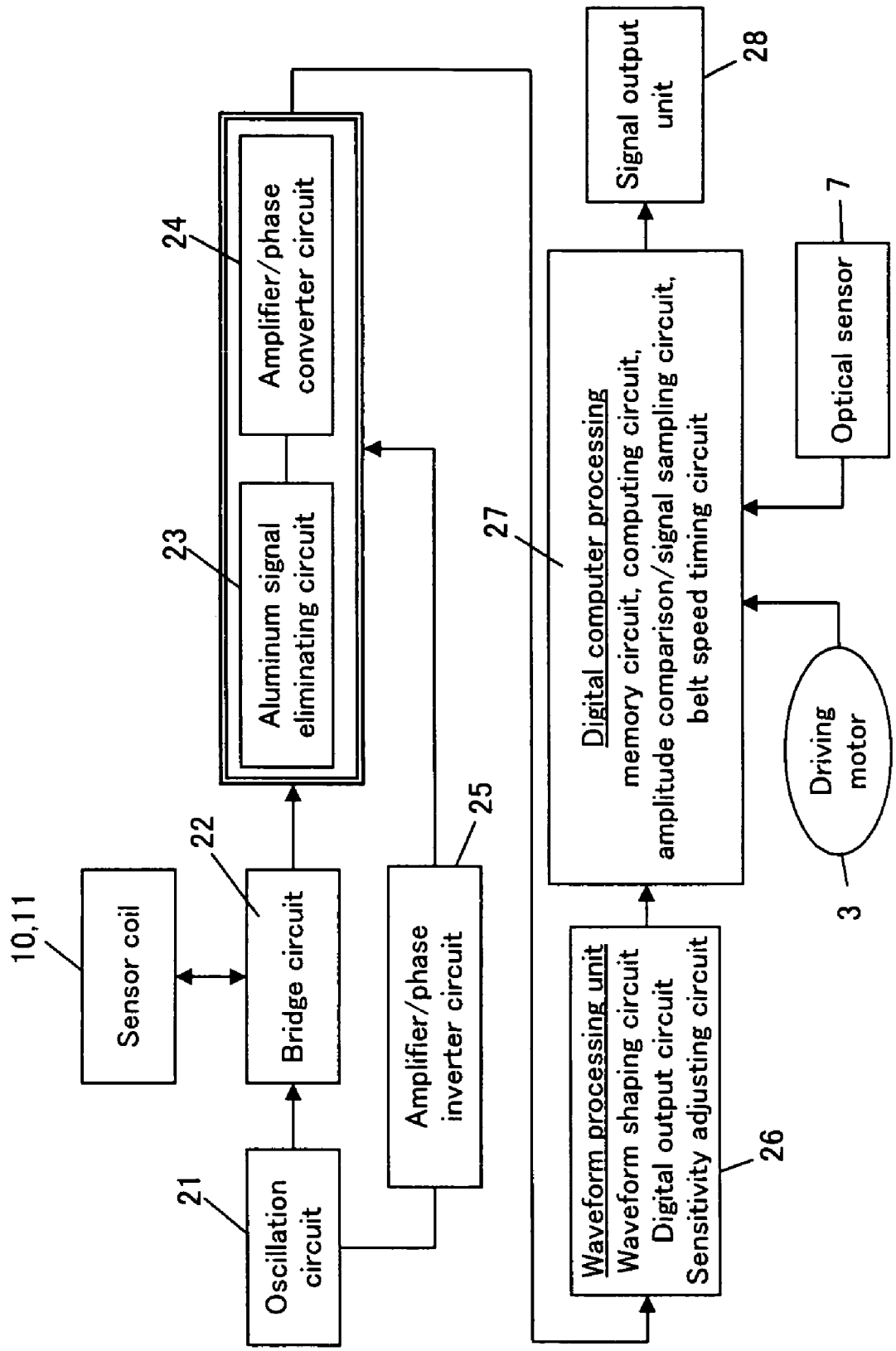
FIG. 4 is a functional block diagram showing the arrangement of a control part 5 in the metallic contaminant detecting apparatus 1.

FIG. 4 is a functional block diagram schematically showing the control part 5. The control part 5 comprises an oscillation circuit 21, a bridge circuit 22, an aluminum signal eliminating circuit 23, an amplifier/phase converter circuit 24, an amplifier/phase inverter circuit 25, a waveform processing unit 26, a digital computer processing unit 27, a signal output unit 28, etc.

The oscillation circuit 21 supplies AC power to the control part 5 and the sensor coils 10 and 11. The oscillation circuit 21 supplies AC power through a transformer. The use of a transformer provides the advantage that the power supply circuit and a measuring part including the sensor coils 10 and 11 and the bridge circuit 22 can be regarded as independent of each other. The bridge circuit 22 receives signals from the sensor coils 10 and 11.

A signal from the bridge circuit 22 is sent to the aluminum signal eliminating circuit 23. The aluminum signal eliminating circuit 23 eliminates a signal from an aluminum packaging material, which is an electrically conductive material, included in the signal from the bridge circuit 22. The signal processing is executed by using a signal from the amplifier/phase inverter circuit 25 as follows. The amplifier/phase inverter circuit 25 takes out a current signal from the oscillation circuit 21, amplifies and phase-inverts the signal.

The aluminum signal eliminating circuit 23 adds together the signal (detection current) from the bridge circuit 22 and the phase-inverted current signal from the amplifier/phase inverter circuit 25 to eliminate the AC power source signal (original current). Then, the aluminum signal eliminating circuit 23 takes out only a signal above a predetermined threshold value to eliminate a noise signal.

Next, the signal output from the aluminum signal eliminating circuit 23 is amplified and subjected to phase converting adjustment processing in the amplifier/phase converter circuit 24 before being output to the waveform processing unit 26. The waveform processing unit 26 waveshapes the input signal, converts it into a digital signal and outputs it to the digital computer processing unit 27 after adjusting the reception sensitivity. It should be noted that the threshold processing provided in the aluminum signal eliminating circuit 23 may be executed in the waveform processing unit 26. In such a case, the threshold processing is performed on a signal converted into a digital signal.

The digital computer processing unit 27 comprises a memory circuit, a computing circuit, an amplitude comparison/signal sampling circuit, a belt speed timing circuit, and so forth. The digital computer processing unit 27 receives information concerning the motor rotational speed from the driving motor 3 to compute the traveling speed of the belt 9. The digital computer processing unit 27 also receives an inspection object signal from the optical sensor 7 to obtain information concerning the passage of the inspection object through the sensor coils 10 and 11.

Thus, the digital computer processing unit 27 receives the digital signal from the waveform processing unit 26 to detect a metallic contaminant that may be contained in the inspection object on the basis of the received digital signal in combination with the above-described belt speed, the inspection object passage signal, etc. If a metallic contaminant is judged to be present, the digital computer processing unit 27 outputs a metallic contaminant signal to the signal output unit 28.

Figure 5:
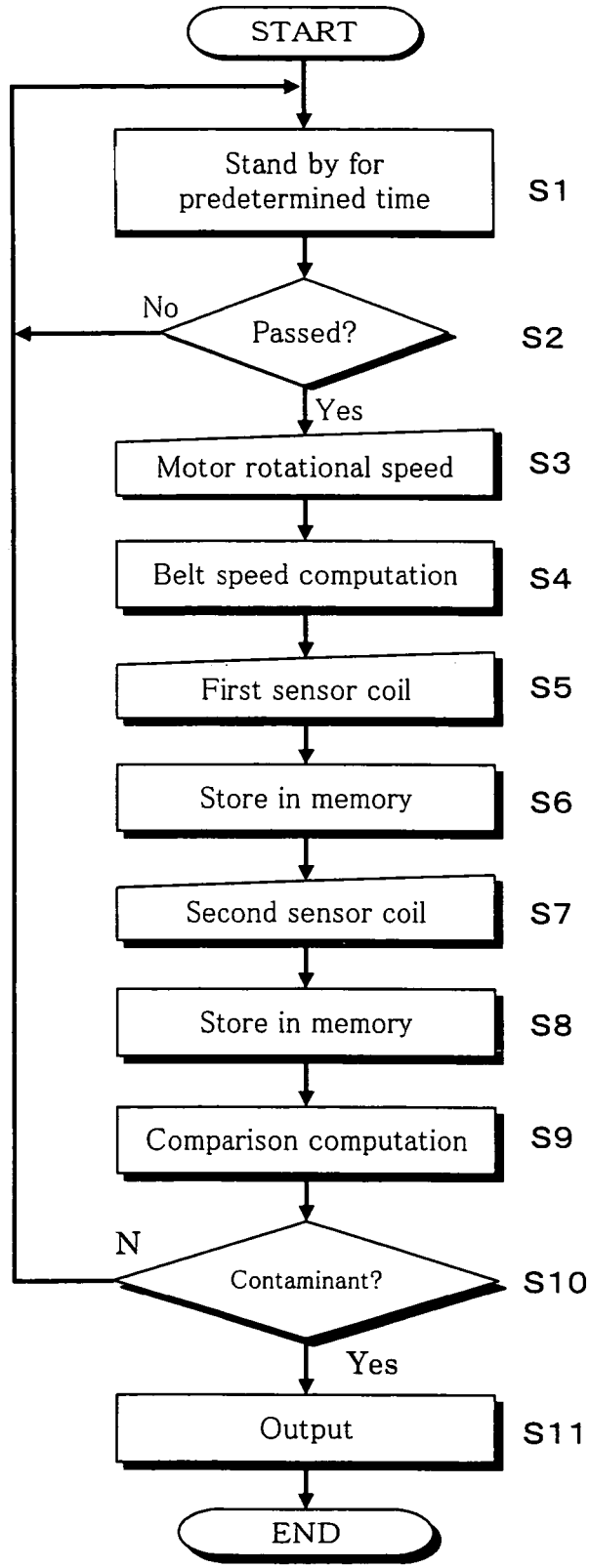
FIG. 5 is a flowchart showing an example of the operation of a digital computer processing unit 27 in the control part 5.
Figure 6:
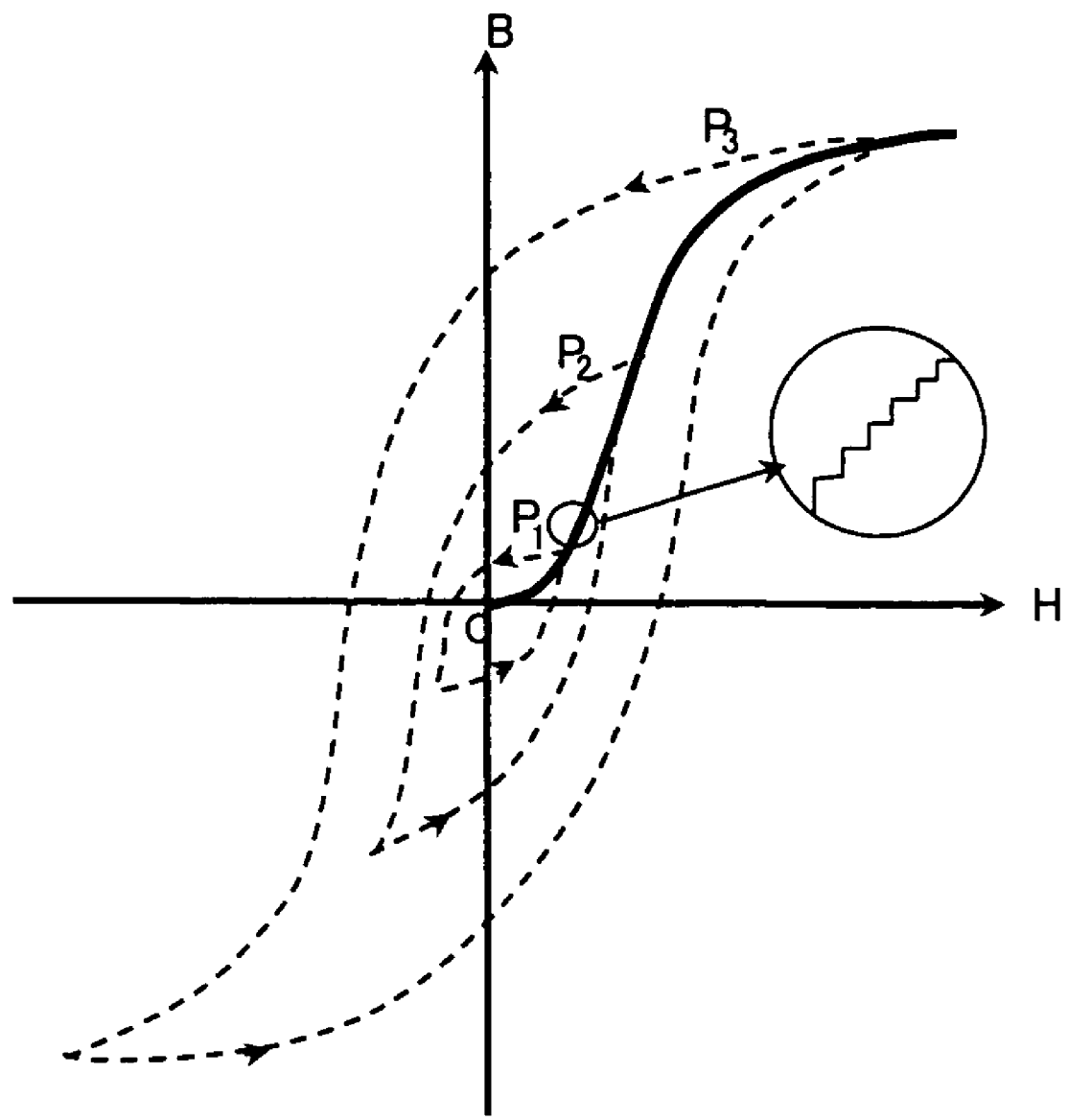
FIG. 6 is a diagram showing B-H characteristics.

FIG. 5 is a flowchart of the processing executed by the digital computer processing unit 27 to perform the detection of a metallic contaminant. The digital computer processing unit 27 constantly makes a judgment about the presence or absence of a metallic contaminant on the basis of the sensing signal from the optical sensor 7. After standing by for a predetermined period of time (S1), the digital computer processing unit 27 checks whether or not a signal from the optical sensor 7 has been received (S2). When an inspection object passes through the optical sensor 7 (see FIG. 2), a signal indicating that the inspection object is passing is output from the optical sensor 7 to the control part 5. The signal is received by the digital computer processing unit 27.

If it is judged that an inspection object is passing ("Yes" at S2), the digital computer processing unit 27 receives the rotational speed of the driving motor 3 (S3). The digital computer processing unit 27 computes the conveying speed of the belt 9 by using the received rotational speed (S4). Thereafter, the digital computer processing unit 27 receives a digital signal concerning the first sensor coil 10 from the waveform processing unit 26 (S5) and stores the received digital signal in the memory region (S6). Similarly, the digital computer processing unit 27 receives a digital signal concerning the second sensor coil 11 (S7) and stores it in the memory region (S8).

The digital computer processing unit 27 makes a comparison between the digital signals of the first and second sensor coils 10 and 11 stored in the memory region (S9) to judge whether or not a contaminant is present in the inspection object (S10). If it is judged that there is no contaminant ("No" at S10), the digital computer processing unit 27 stands by for a predetermined period of time (S1). If it is judged that there is a contaminant ("Yes" at S10), the digital computer processing unit 27 outputs a signal indicating the presence of a contaminant (S11). Thus, a series of processing operations for judging the presence or absence of a metallic contaminant are executed.

(Description of Detection Circuit)

Figure 9:
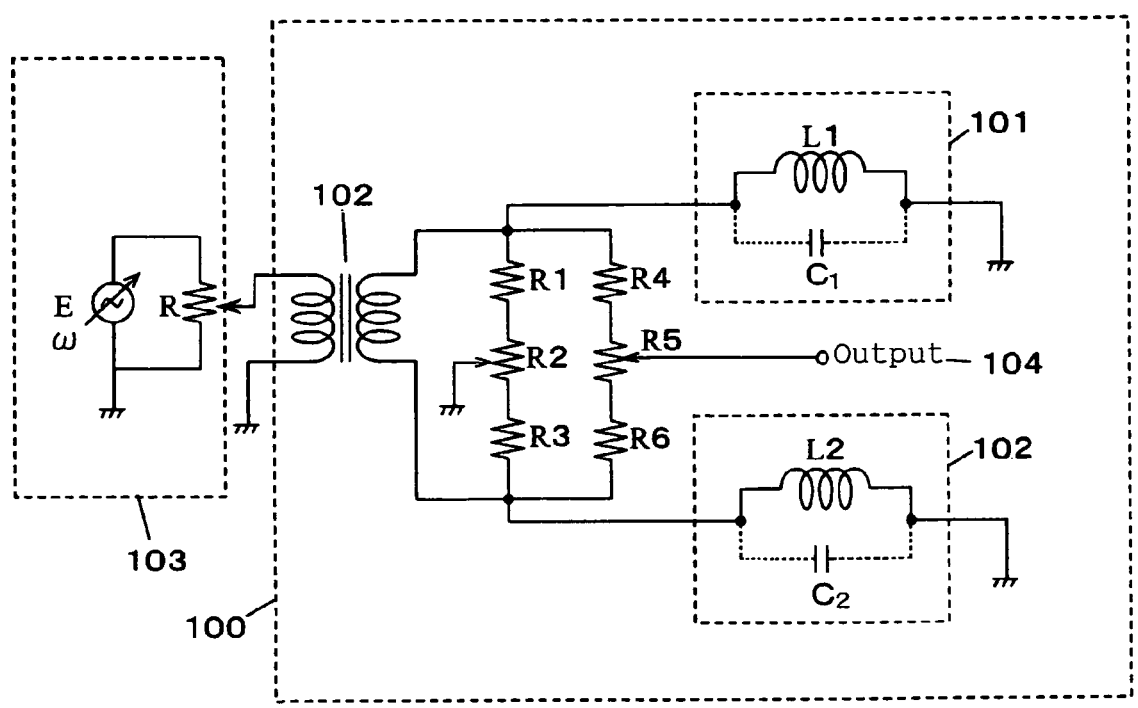
FIG. 9 shows the outline of a detection circuit in embodiment 1 that contains sensor coils.

FIG. 9 shows a detection circuit 100. The detection circuit 100 will be explained below, together with the above-described oscillation circuit, bridge circuit and sensor coil 10. In actuality, the above-described sensor coil 10 serves as one arm of a bridge circuit 101. In the embodiment 1, two sensor coils 10a and 10b are provided. The sensor coil 10 is supplied with an alternating current to radiate an alternating magnetic field directly to the vicinity of the coil detection surface. The sensor coil 10 detects a turbulent magnetic field when an inspection object 8 having a small metal fragment disorders the orientation of the alternating magnetic field, and outputs a contaminant detecting signal.

The detection circuit 100 has a bridge circuit 101. The sensor coil 10 serves as one arm of the unbalanced bridge circuit 101. The bridge circuit 101 is supplied with an electric energy of frequency $\omega$ from a variable-frequency power source 103 through a matching transformer 103. The bridge circuit 101, including the sensor coil 10, is isolated from the variable-frequency power source 103 by the matching transformer 102.

The detection circuit 100 has a plurality of resistors R1 to R6 connected in series or in parallel, as illustrated in the figure. One end of the sensor coil 10 is connected to one end of the resistors. The other end of the sensor coil 10 is grounded. When no metallic contaminant is detected in the normal state, the sensor coils 10a and 10b are balanced with each other (see FIG. 10). Consequently, no signal is output from an output terminal 104. When a metallic contaminant contained in an inspection object passes between the sensor coils 10a and 10b, the balanced state is changed, and a signal is output from the output terminal 104.

Figure 10:
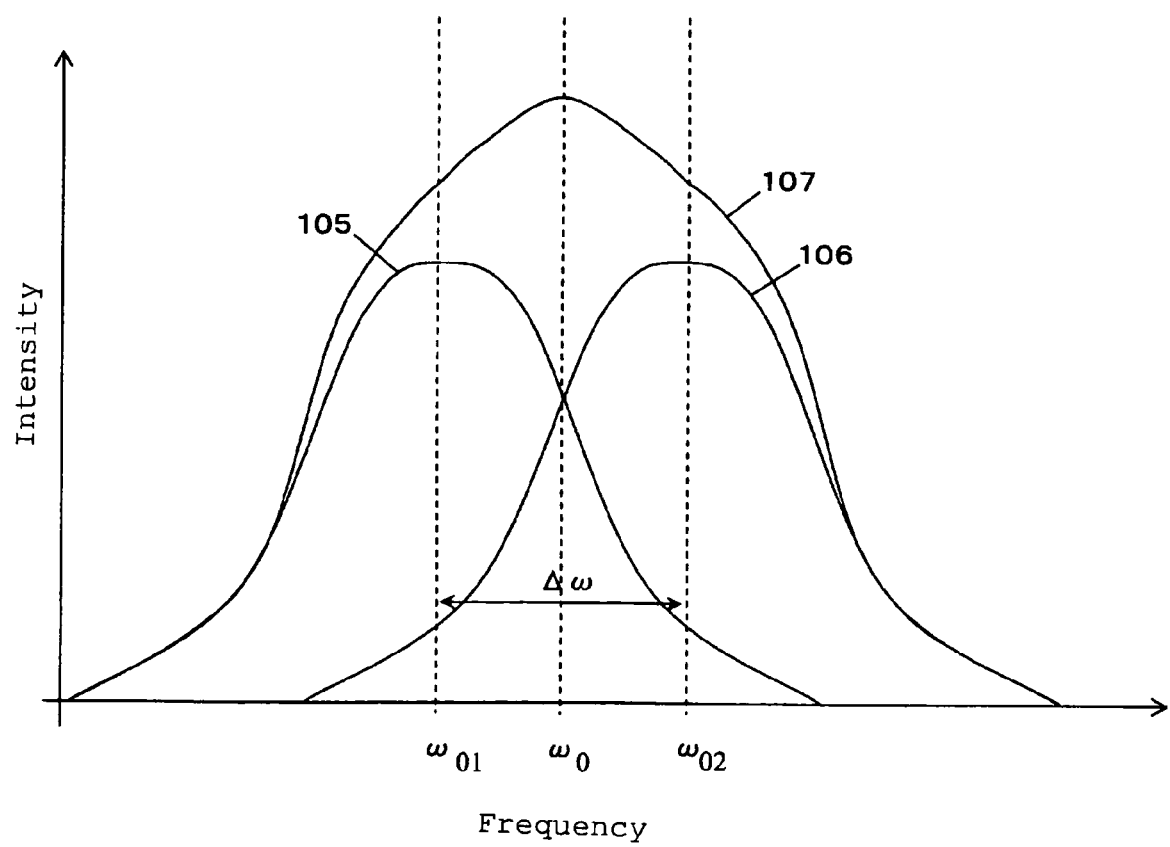
FIG. 10 is a diagram showing the frequency characteristics of the detection circuit in embodiment 1.
Figure 12:
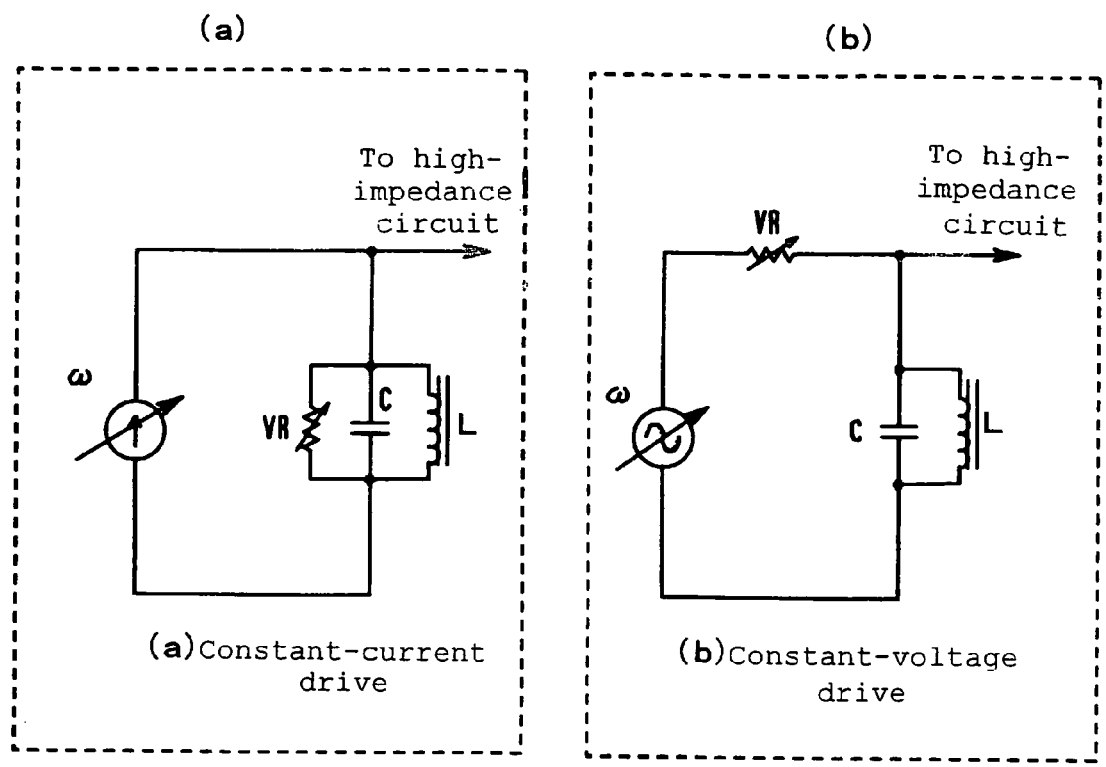
FIGS. 12(a) and (b) are simplified circuit diagrams of the equivalent circuit shown in FIG. 11(b).

Alternatively, the detection circuit 100 may be set so that a signal is output from the output terminal 104 even when no metallic contaminant is detected. In such a case, the bridge circuit 101 is unbalanced. FIG. 10 shows the frequency characteristics of the bridge circuit 101 including the sensor coils 10a and 10b. The abscissa axis is a frequency axis representing frequency. The ordinate axis is an axis representing the intensity of wave. The sensor coils 10a and 10b comprise the same inductance, but are less likely to operate at the same frequency because of an accuracy error in the manufacturing process.

The detection circuit 100 is set to obtain a high Q-value by supplying a power of low frequency in the neighborhood of 7 kHz and changing the frequency of the supplied power and the value of the resistance (R1 to R6), as has been stated above in connection with the principle. Assuming that the center frequencies of the sensor coils 10a and 10b are $\omega_{01}$ and $\omega_{02}$, respectively, they are separate from each other by $\Delta\omega$ ($=|\omega_{01}-\omega_{02}|$). In FIG. 10, a graph 105 shows the characteristics of the sensor coil 10*a*, and a graph 106 shows the characteristics of the sensor coil 10*b*. A graph 107 shows the sum of the characteristics of the sensor coils 10*a* and 10*b*. The center frequency of the graph 107 is $\omega_0$.

When no metallic contaminant passes near the sensor coil 10, the detection circuit is in the state of $\omega_0$. When a metallic contaminant passes near the sensor coil 10, it affects the magnetic field of the sensor coil 10, causing the frequencies $\omega_{01}$ and $\omega_{02}$ of the sensor coils 10*a* and 10*b* to change. Consequently, the overall center frequency $\omega_0$ of the detection circuit also changes. Accordingly, a detection signal is output from the output terminal 104 of the detection circuit.

Thus, the use of two circuits enables a metallic contaminant to be detected with high sensitivity because the center frequency $\omega_0$ changes in response to a small change in the magnetic field of the sensor coil 10. It should be noted that the detection circuit 100 may have only the sensor coil 10*a* to detect a metallic contaminant.

[Embodiment 2] (Crossed Arrangement of Sensor Coils)

Figure 7:
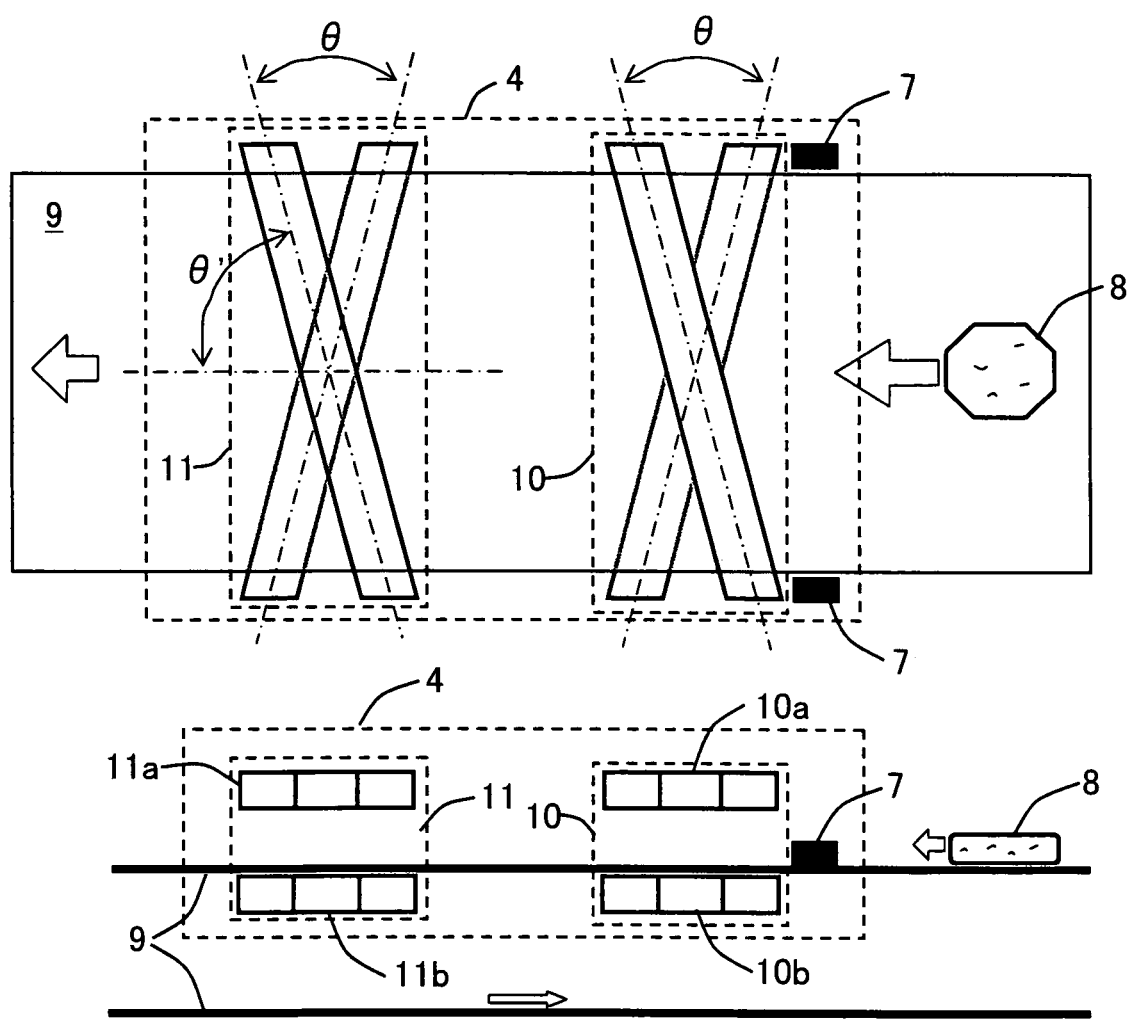
FIG. 7 contains a schematic plan view and a schematic front view, which show an example of the arrangement of sensor coils in embodiment 2.

FIG. 7 is a diagram showing an embodiment in which the sensor coils are disposed to cross each other. The embodiment 2 is basically the same as the above-described embodiment 1. Only a part in which the embodiment 2 differs from the embodiment 1 will be described below. A detailed description of the same portions as those of the embodiment 1 is omitted. In the embodiment 2, the sensor coils are disposed to cross each other.

More specifically, the sensor coil 10*a* and the sensor coil 10*b*, which constitute the first sensor coil, are disposed to cross each other at a predetermined angle θ (as seen from above). The sensor coils 10*a* and 10*b* are disposed to extend horizontally in parallel to the belt 9. The sensor coils 10*a* and 10*b* intersect the conveying direction of the belt 9 at an angle of (π−θ)/2 (=θ') and an angle of (π+θ)/2 (=θ'+θ), respectively (see FIG. 7). It should be noted that the arrangement of the sensor coils 10*a* and 10*b* may be reverse to the above.

The arrangement of the sensor coil 11*a* and the sensor coil 11*b*, which constitute the second sensor coil, is similar to the arrangement of the sensor coils 10*a* and 10*b*. Therefore, a description thereof is omitted. If the sensor coils are disposed to cross each other in this way, a metallic contaminant contained in an inspection object can be detected favorably no matter which direction the inspection object faces when it flows between the sensor coils.

For instance, many of metallic contaminants have an elongate configuration. If such an elongate metallic contaminant passes between the sensor coils in the state of extending parallel to the sensor coils or in the state of standing upright, the detection sensitivity is degraded. In such a case, if the sensor coils are disposed to cross each other, the metallic contaminant can be detected favorably no matter which direction it faces when passing between the sensor coils.

[Embodiment 3] (Arrangement of Magnet Booster)

Figure 8:
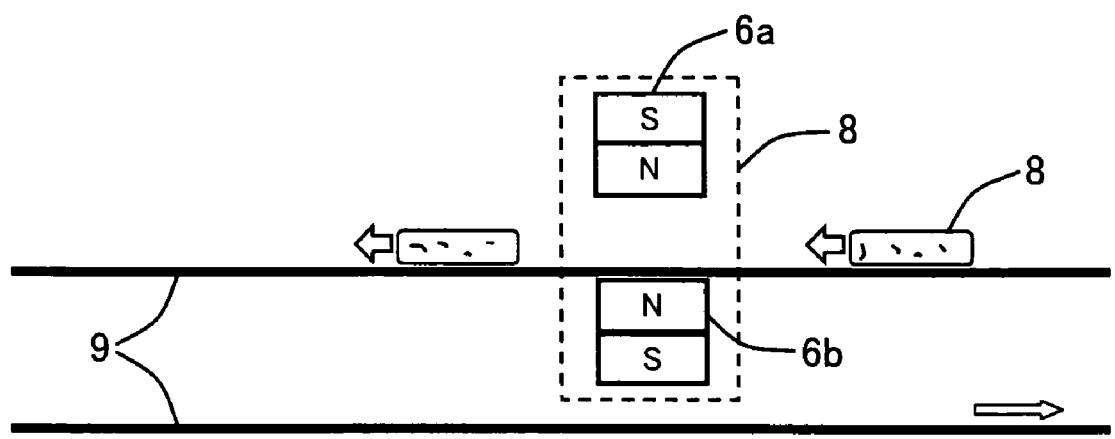
FIG. 8 is a diagram showing a structural example of a magnet booster 6 in embodiment 3.

The embodiment 3 is basically the same as the embodiment 1 or 2. Only a part in which the embodiment 3 differs from the embodiment 1 or 2 will be described below. A detailed description of the same portions as those of the embodiment 1 or 2 is omitted. FIG. 8 is a diagram showing the arrangement of the magnet booster 6. The magnet booster 6 comprises a magnet element 6*a* and a magnet element 6*b*. The magnet elements 6*a* and 6*b* are installed facing each other vertically across the belt 9. The magnet elements 6*a* and 6*b* are disposed such that their like magnetic poles N face toward the belt 9. The magnet booster 6 is arranged so that an inspection object 8 passes between the magnet element 6*a* and the magnet element 6*b*.

It should be noted that each of the magnet elements 6*a* and 6*b* may comprise a plurality of magnet elements. Further, the magnet elements 6*a* and 6*b* may be arranged or installed in any form, provided that the magnet elements 6*a* and 6*b* are disposed at both sides of the conveyance path along which an inspection object is conveyed, and their like magnetic poles face toward the conveyance path. If the magnet booster 6 is arranged as stated above, a metallic contaminant mixed in the inspection object passing through the magnet booster 6 is caused to fall in the conveying direction of the belt 9 by the repulsion between the magnetic fields of the magnet elements 6*a* and 6*b* on both sides. Consequently, it becomes easy to detect the metallic contaminant at the sensor storage part 4.

[Embodiment 4] (Analysis of Frequency and Waveform)

The embodiment 4 is basically the same as the embodiments 1 through 3. Only a part in which the embodiment 4 differs from the embodiments 1 through 3 will be described below. A detailed description of the same portions as those of the embodiments 1 through 3 is omitted. The digital computer processing unit 27 shown in FIG. 4 may analyze the frequency and waveform of a digital signal by using a technique such as Fourier transform to identify a matter to which the frequency and waveform of the digital signal is attributable, thereby detecting a metallic contaminant. For this purpose, it is necessary to prepare analytic data concerning the frequency and waveform of the digital signal.

Further, the digital computer processing unit 27 may also perform elimination of the signal derived from the AC power source (AC excitation power source), which is executed in the aluminum signal eliminating circuit 23. The signal input to the aluminum signal eliminating circuit 23 is converted into a digital signal and input to the digital computer processing unit 27. The digital signal is separated for each frequency to eliminate a signal attributable to the AC power source, noise, etc. A noise signal from the inspection object may also be eliminated through the analysis of frequency and waveform.

[Embodiment 5]

FIGS. 13 to 16 show an actual structural example of the circuit of the above-described metallic contaminant detecting apparatus 1. The circuit signal in the embodiment 5 is processed in an analog circuit. It is also possible to digitize the signal output from the bridge circuit 22 and to process digitally all or a part of the following operations by a computer, i.e. the above-described aluminum signal elimination, phase conversion and wave-shaping processing, and sensitivity adjustment.

Figure 13:
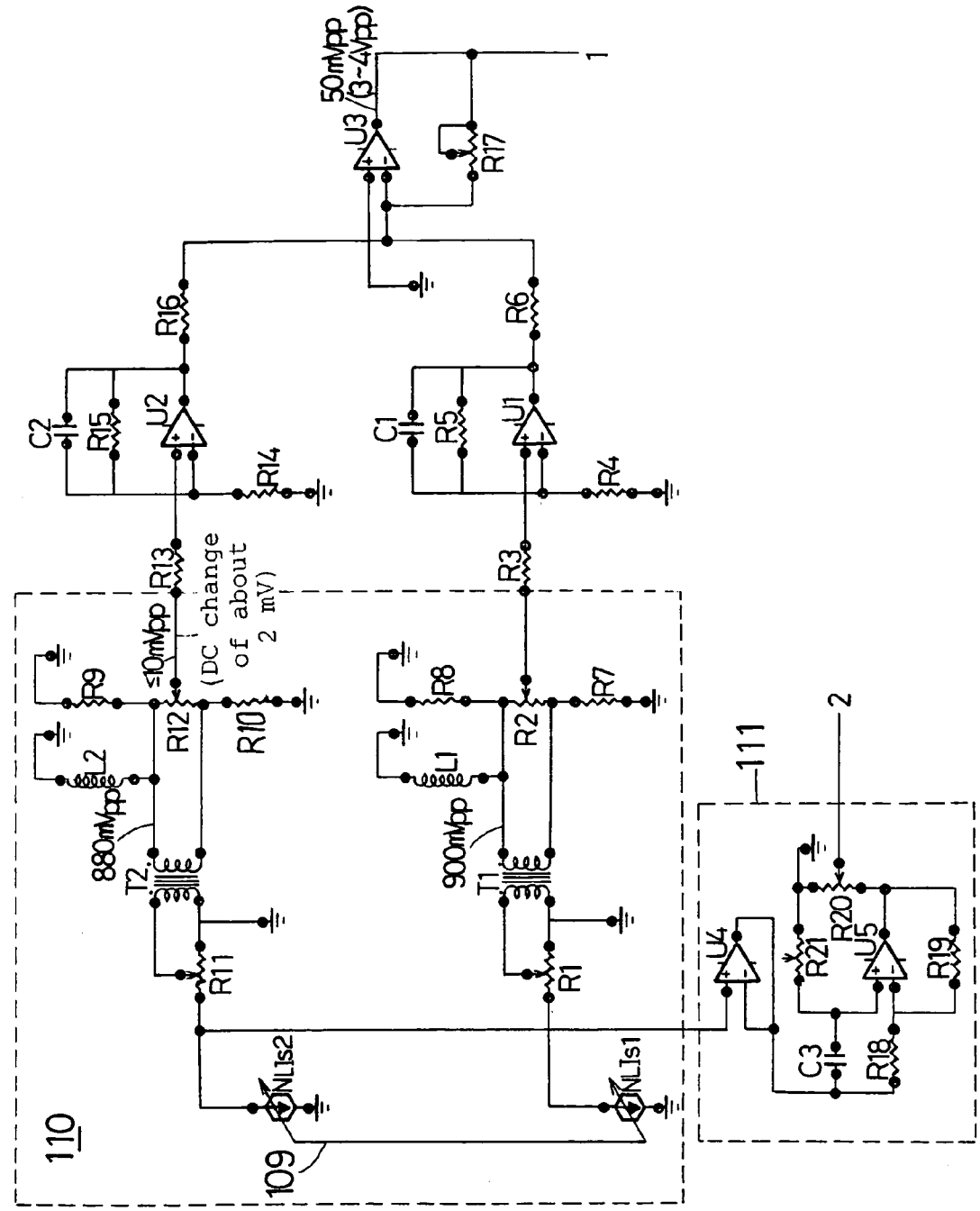
FIG. 13 shows a circuit example according to embodiment 6.

The following is a description of only the outline of essential portions of the circuit. FIG. 13 shows an AC power source 109, a sensor circuit 110 and a phase converter circuit 111. The AC power source 109 corresponds to the oscillation circuit 21 shown in FIG. 4. Similarly, the sensor circuit 110 is a circuit comprising a combination of the sensor coils 10 and 11 and the bridge circuit 22. The phase inverter circuit 111 corresponds to the amplifier/phase inverter circuit 25 (see FIG. 4).

Figure 14:
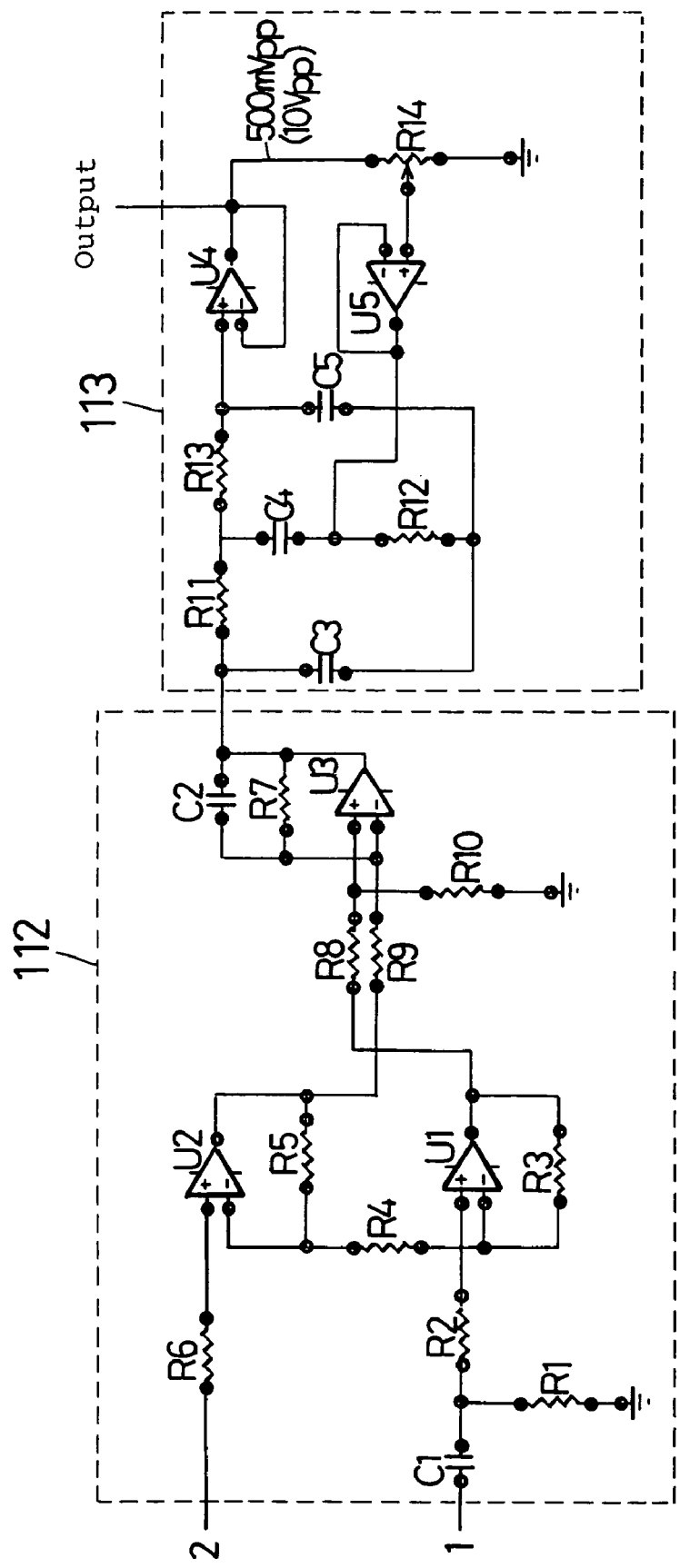
FIG. 14 shows a circuit example according to embodiment 6.

FIG. 14 shows a differential amplifier circuit 112 and a waveform shaping circuit 113. The differential amplifier circuit 112 corresponds to a combination of the aluminum signal eliminating circuit 23 and the amplifier/phase converter circuit 24, and the waveform shaping circuit 113 corresponds to the waveform processing unit 26 (see FIG. 4). The sensor circuit 110 receives a signal from an inspection object 8. The signal is output to an output terminal "1" and input to the differential amplifier circuit 112 from "1" in FIG. 14.

The phase converter circuit 111 shown in FIG. 13 takes out a signal from the AC power source 109, adjusts the phase thereof and outputs it from "2", which is "2" in FIG. 14. Thus, the signal is input to the differential amplifier circuit 112. The differential amplifier circuit 112 receives the signal output from the sensor circuit 110 and removes the signal derived from the AC power source 109 from the received signal. Only the signal derived from the inspection object is taken out from the differential amplifier circuit 112 and output after being wave-shaped by the circuit 113.

Figure 15:
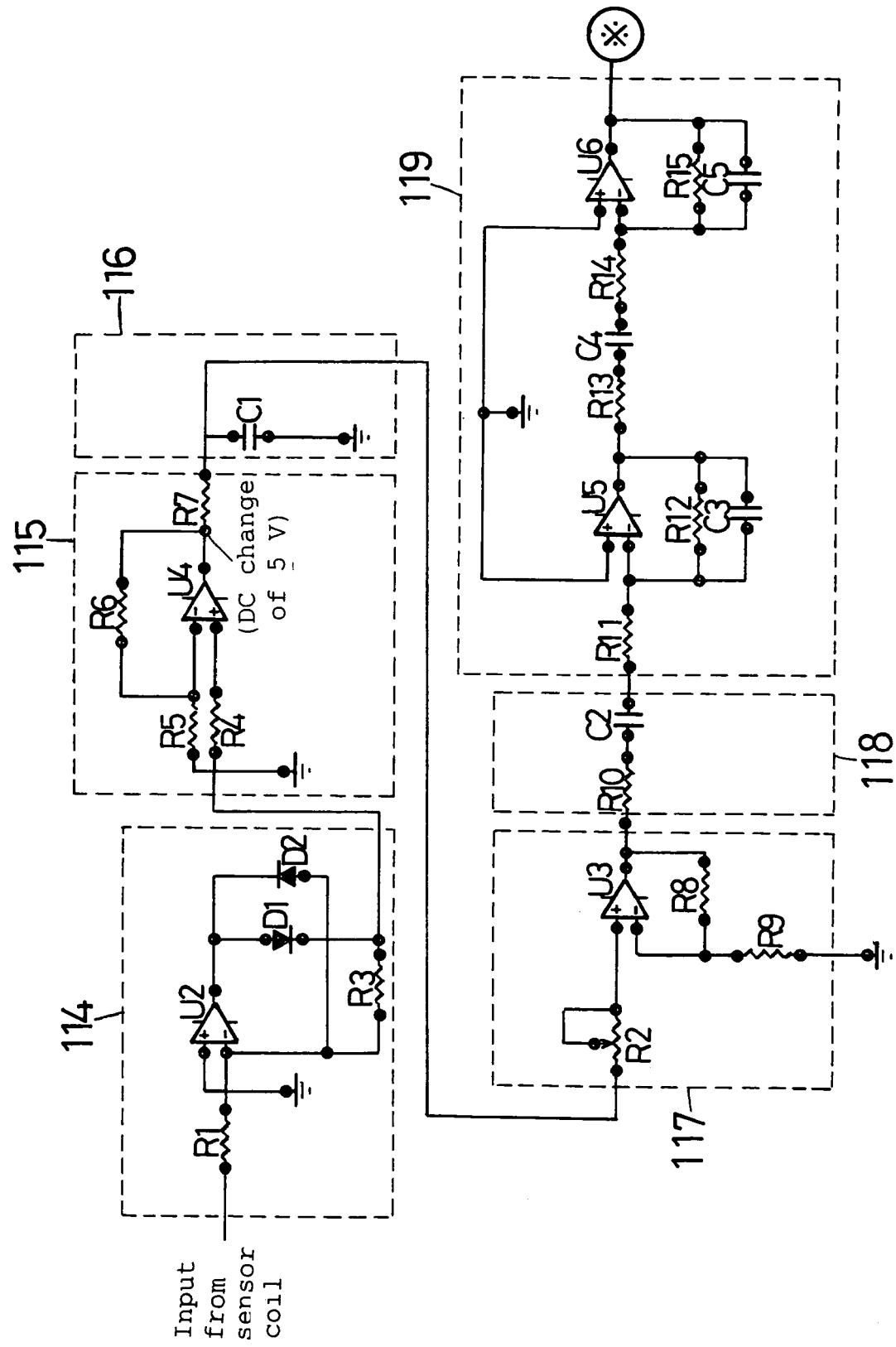
FIG. 15 shows a circuit example according to embodiment 6.
Figure 16:
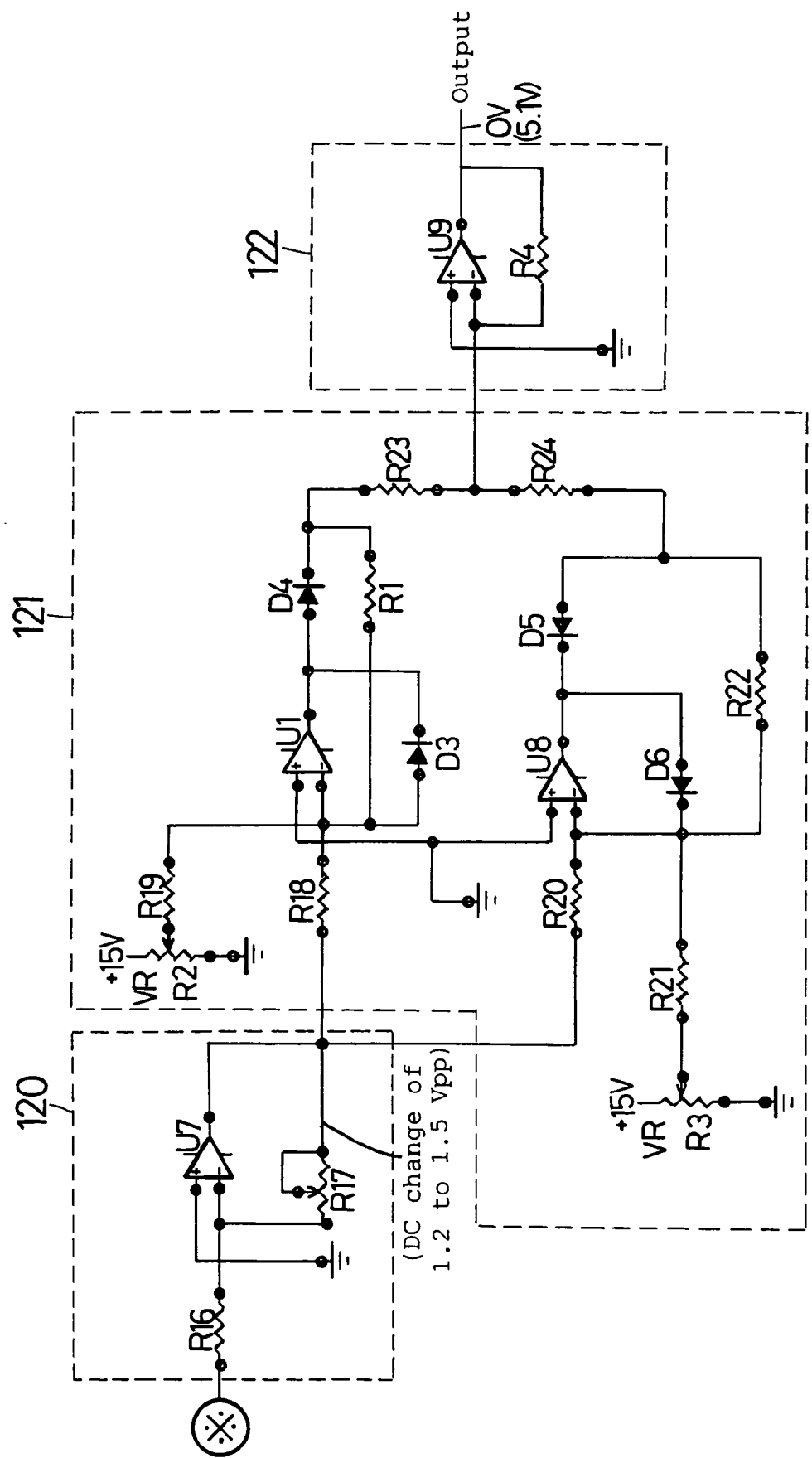
FIG. 16 shows a circuit example according to embodiment 6.
Figure 17:
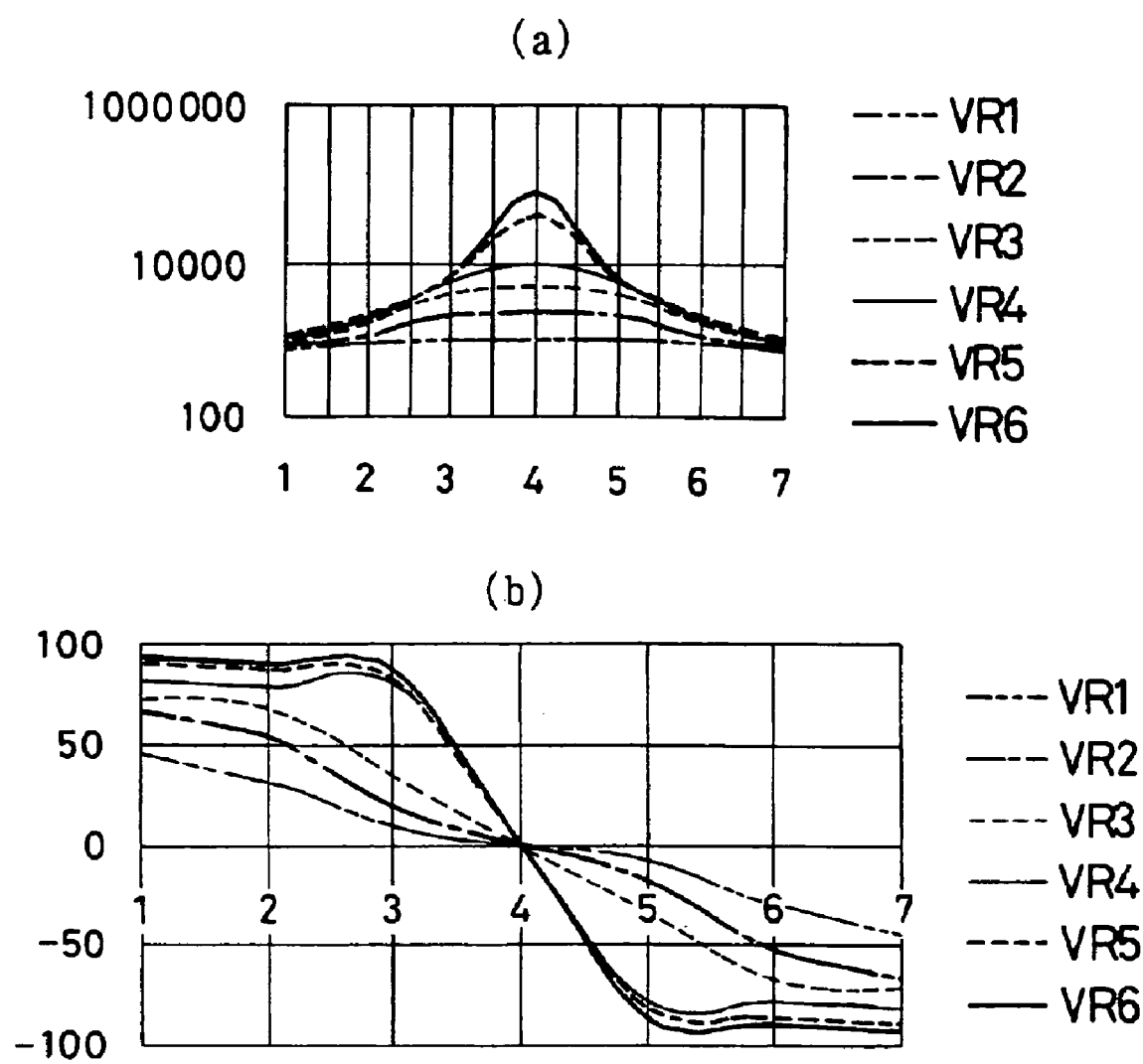
FIGS. 17(a) and (b) are graphs showing the characteristics of the circuit illustrated in FIG. 11.

FIGS. 15 and 16 show a circuit for analyzing the signal from the inspection object, which executes analog processing. This part may be digitized to perform computer processing. FIG. 15 shows a rectifying circuit 114, an amplifier circuit 115, a rectifying circuit 116, an amplifier circuit 117, a DC power cut-off circuit 118, and a waveform processing circuit 119. FIG. 16 shows a sensitivity adjusting circuit 120, a waveform threshold circuit 121, and an amplifier circuit 121. The rectifying circuits 114 and 116 are for rectifying the signal and shaping the waveform. The amplifier circuits 115, 117 and 122 are for amplifying the signal. The DC power cut-off circuit 118 is for cutting off the DC signal component contained in the signal. The sensitivity adjusting circuit 120 is for adjusting the detection sensitivity for the inspection object. A detection sensitivity can be set by changing the value of resistance of the sensitivity adjusting circuit 120. The waveform threshold circuit 121 is for adjusting the level of the output signal.

INDUSTRIAL APPLICABILITY

The present invention detects a magnetic metallic contaminant mixed in an inspection object wrapped in an electrically conductive packaging material formed by vacuum deposition of aluminum or made of aluminum foil or the like. The present invention is applicable to the field of detecting magnetic metallic contaminants mixed in inspection objects such as frozen food products, grain or other food product materials, pharmaceuticals, and materials for industrial use.

The invention claimed is:

1. A metallic contaminant detecting method comprising the steps of:
conveying an inspection object contained in a package along a conveyance path to detect a metallic contaminant accidentally mixed in said inspection object during a manufacturing process; and
detecting step of detecting the metallic contaminant mixed in said inspection object by generating a magnetic field from a detecting element provided in an intermediate portion of said conveyance path, said detecting element having a coil comprising a core and a conductor wound around said core;
generating a small magnetic field by applying a voltage to said coil or supplying an electric current to said coil, and detecting a detection magnetic field generated from said metallic contaminant in response to said small magnetic field as a detection voltage or a detection current of said coil, and then outputting a detection signal; and
analyzing said detection signal to identify said metallic contaminant;
wherein said small magnetic field is created by applying a small voltage to said coil or supplying a small electric current to said coil and using a non-linear portion of magnetic field characteristics of said core constituting said coil, in which a magnetic field (H) and a magnetic flux density (B) of the non-linear portion are small values of about zero; and
said coil operates at a frequency in a range of several hundred Hz to several ten kHz.

2. The metallic contaminant detecting method according to claim 1, wherein said detecting element outputs said detection signal when said detection magnetic field affects said small magnetic field to change said voltage applied to said coil or said current supplied to said coil.

3. The metallic contaminant detecting method according to claim 1 or 2, wherein said inspection object has a package made of an electrically conductive material, and
wherein an eddy current induced in said electrically conductive material by said small magnetic field is so small that the eddy current does not substantially affect a voltage or an electric current flowing through said coil.

4. The metallic contaminant detecting method according to claim 1 or 2, wherein said signal analyzing step comprises:
adding together said detection signal and a phase-inverted signal obtained by phase-inverting an AC excitation power source causing said coil to generate said small magnetic field, thereby eliminating a signal derived from said AC excitation power source from said detection signal; and
taking out a signal above a predetermined threshold value, thereby separating a magnetic field signal derived from said inspection object from said detection signal.

5. The metallic contaminant detecting method according to claim 1 or 2, wherein said metallic contaminant detecting step comprises a first detecting step and a second detecting step,
said first detecting step and said second detecting step being arranged so that said inspection object passes through said second detecting step after passing through said first detecting step,
wherein said detection signal that is detected simultaneously by said first detecting step and said second detecting step is eliminated by said signal analyzing step.

6. The metallic contaminant detecting method according to claim 1 or 2, further comprising:
magnetizing said metallic contaminant in said conveyance path by a magnet booster comprising magnet elements before said metallic contaminant detecting step.

7. The metallic contaminant detecting method according to claim 1 or 2, wherein said package is made of a paramagnetic or diamagnetic metal.

8. The metallic contaminant detecting method according to claim 1 or 2, wherein said metallic contaminant is an austenite or martensite stainless steel material.

9. The metallic contaminant detecting method according to claim 1 or 2, wherein said detecting element has a first coil and a second coil and comprises a first circuit that is an oscillation circuit including said first coil, and a second circuit that is an oscillation circuit including said second coil,
wherein said first circuit and said second circuit are connected in parallel.

10. The metallic contaminant detecting method according to claim 9, wherein said first coil for detecting one surface of said inspection object and said second coil for detecting another surface of said inspection object opposite to said one surface are disposed at a predetermined angle with respect to a traveling direction of said inspection object, and wherein said first coil and said second coil are disposed with a predetermined angle with respect to each other.

11. A metallic contaminant detecting apparatus comprising:

conveying means having a conveyance path for conveying an inspection object contained in a package to detect a metallic contaminant accidentally mixed in said inspection object during a manufacturing process; and metallic contaminant detecting means for detecting the metallic contaminant mixed in said inspection object by generating a magnetic field from a detecting element provided in an intermediate portion of said conveyance path, said detecting element having a coil comprising a core and a conductor wound around said core;

detection signal outputting means for generating a small magnetic field by applying a voltage to said coil or supplying an electric current to said coil, and for detecting a detection magnetic field generated from said metallic contaminant in response to said small magnetic field as a detection voltage or a detection current of said coil and outputting a detection signal; and a signal analyzing means for analyzing said detection signal to identify said metallic contaminant;

wherein said small magnetic field is created by applying a small voltage to said coil or supplying a small electric current to said coil to use a non-linear portion of magnetic field characteristics of said core constituting said coil, in which a magnetic field (H) a magnetic flux density (B) of the non-linear portion are small values of about zero; and said coil operates at a frequency in a range of from several hundred Hz to several ten kHz.

12. The metallic contaminant detecting apparatus according to claim 11, wherein said detecting element outputs said detection signal when said detection magnetic field affects said small magnetic field to change said voltage applied to said coil or said current supplied to said coil.

13. The metallic contaminant detecting apparatus according to claim 11 or 12, wherein said inspection object has a package made of an electrically conductive material, and wherein an eddy current induces in said electrically conductive material by said small magnetic field is so small that the eddy current does not substantially affect a voltage or an electric current flowing through said coil.

14. The metallic contaminant detecting apparatus according to claim 11 or 12, wherein said signal analyzing means adds together said detection signal and a phase-inverted signal obtained by phase-inverting an AC excitation power source causing said coil to generate said small magnetic field, thereby eliminating a signal derived from said AC excitation power source from said detection signal, and takes out a signal above a predetermined threshold value, thereby separating a magnetic field signal derived from said inspection object from said detection signal.

15. The metallic contaminant detecting apparatus according to claim 11 or 12, wherein said metallic contaminant detecting means comprises a first detecting means and a second detecting means, said first detecting means and said second detecting means being arranged so that said inspection object passes through said second detecting means after passing through said first detecting step, wherein said detection signal that is detected simultaneously by said first detecting means and said second detecting means is eliminated by said signal analyzing means.

16. The metallic contaminant detecting apparatus according to claim 11 or 12, further comprising:

a magnet booster disposed in said conveyance path upstream of said metallic contaminant detecting means, said magnet booster comprising magnet elements.

17. The metallic contaminant detecting apparatus according to claim 13 or 14, wherein said package is made of a paramagnetic or diamagnetic metal.

18. The metallic contaminant detecting apparatus according to claim 11 or 12, wherein the electric current or voltage supplied to said coil has a frequency in a range of from several hundred Hz to several ten kHz, and said frequency changes when said metallic contaminant passes near said coil.

19. The metallic contaminant detecting apparatus according to claim 11 or 12, wherein said detecting element has a first coil and a second coil and comprises a first circuit that is an oscillation circuit including said first coil, and a second circuit that is an oscillation circuit including said second coil, wherein said first circuit and said second circuit are connected in parallel.

20. The metallic contaminant detecting apparatus according to claim 19, wherein said first coil for detecting one surface of said inspection object and said second coil for detecting another surface of said inspection object opposite to said one surface are disposed at a predetermined angle with respect to a traveling direction of said inspection object, and wherein said first coil and said second coil are disposed with a predetermined angle with respect to each other.

* * * * *